(12) United States Patent
Denyer et al.

(10) Patent No.: US 12,383,683 B1
(45) Date of Patent: Aug. 12, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,497

(22) Filed: Aug. 29, 2024

(51) Int. Cl.
*A61M 5/32* (2006.01)
*A61M 5/315* (2006.01)

(52) U.S. Cl.
CPC ...... *A61M 5/3202* (2013.01); *A61M 5/31525* (2013.01); *A61M 5/31526* (2013.01);
(Continued)

(58) Field of Classification Search
CPC ........ A61M 2005/3208; A61M 5/3202; A61M 5/31525; A61M 5/31526; A61M 5/3158; A61M 5/31593; A61M 5/31595
See application file for complete search history.

(56) References Cited

U.S. PATENT DOCUMENTS 4,989,307 A * 2/1991 Sharpe ................ A61M 5/3205
128/917
5,069,667 A * 12/1991 Freundlich .......... A61M 5/3205
604/110

(Continued)

FOREIGN PATENT DOCUMENTS

FR          2024089 A5 * 8/1970 ........ A61M 5/31595
WO  WO-2014060369 A1 * 4/2014 ............. A61M 5/20
(Continued)

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.
(Continued)

*Primary Examiner* — Bhisma Mehta
*Assistant Examiner* — Adam J. Cermak
(74) *Attorney, Agent, or Firm* — Fish & Richardson P.C.

(57) ABSTRACT

A medicament delivery device includes: a body; a needle cover axially movable between an extended position and a retracted position; a medicament delivery mechanism including a plunger and a drive member configured to move the plunger to dispense a medicament; an actuation member configured to be actuated relative to the body; and a ratchet mechanism coupled to the medicament delivery mechanism and sequentially movable between a first configuration, second configuration and third configuration, wherein the actuation member and ratchet mechanism are arranged such that: a first actuation of the actuation member moves the ratchet mechanism from the first configuration to the second configuration to cause a first dose of the medicament to be dispensed, and a second actuation of the actuation member, subsequent to the first actuation, moves the ratchet mechanism from the second configuration to the third configuration to cause a second dose of the medicament to be dispensed.

19 Claims, 23 Drawing Sheets

(52) U.S. Cl.
CPC ...... *A61M 5/3158* (2013.01); *A61M 5/31593* (2013.01); *A61M 5/31595* (2013.01)

(56) References Cited

U.S. PATENT DOCUMENTS

| | | | | |
|---|---|---|---|---|
| 5,092,462 | A * | 3/1992 | Sagstetter | A61B 50/362 D34/1 |
| 5,356,385 | A * | 10/1994 | Latini | A61M 5/3213 604/110 |
| 6,224,567 | B1 * | 5/2001 | Roser | A61M 5/30 604/218 |
| 8,376,993 | B2 * | 2/2013 | Cox | A61M 5/31545 604/110 |
| 2013/0096513 | A1 * | 4/2013 | Smith | A61M 5/31583 604/211 |
| 2015/0265776 | A1 * | 9/2015 | Beek | A61M 5/20 604/211 |
| 2016/0129188 | A1 * | 5/2016 | Kiilerich | A61M 5/31555 604/228 |
| 2017/0246396 | A1 * | 8/2017 | Wei | A61M 5/2033 |
| 2020/0001014 | A1 * | 1/2020 | Holmqvist | A61M 5/31585 |
| 2021/0162137 | A1 * | 6/2021 | Hagihira | A61M 5/3205 |
| 2021/0236714 | A1 * | 8/2021 | Limaye | A61M 5/3205 |
| 2022/0288299 | A1 * | 9/2022 | Limaye | A61M 5/002 |
| 2023/0001101 | A1 * | 1/2023 | Larsen | A61M 5/3202 |
| 2023/0277769 | A1 * | 9/2023 | Chang | A61M 5/2033 604/136 |
| 2025/0018119 | A1 * | 1/2025 | Lin | A61M 5/2033 |
| 2025/0041529 | A1 * | 2/2025 | Kwolek | A61M 5/31595 |

FOREIGN PATENT DOCUMENTS

| | | | | |
|---|---|---|---|---|
| WO | WO-2014198858 A1 * | 12/2014 | .......... | A61M 5/2033 |
| WO | WO-2018146589 A2 * | 8/2018 | ........ | A61M 5/31501 |
| WO | WO-2018215271 A1 * | 11/2018 | .......... | A61M 5/2033 |
| WO | WO-2021122192 A1 * | 6/2021 | ........ | A61M 5/31501 |
| WO | WO-2021122196 A1 * | 6/2021 | ........ | A61M 5/31515 |
| WO | WO-2022023011 A1 * | 2/2022 | .......... | A61M 5/2033 |
| WO | WO-2022117671 A1 * | 6/2022 | .......... | A61M 5/2033 |
| WO | WO-2022117683 A1 * | 6/2022 | ........ | A61M 5/31571 |
| WO | WO-2022175241 A1 * | 8/2022 | .............. | A61M 5/20 |
| WO | WO-2022175242 A1 * | 8/2022 | ........ | A61M 5/31595 |
| WO | WO-2022175245 A1 * | 8/2022 | .............. | A61M 5/20 |
| WO | WO-2022175246 A1 * | 8/2022 | .............. | A61M 5/002 |
| WO | WO-2022175247 A1 * | 8/2022 | .......... | A61M 5/2033 |

OTHER PUBLICATIONS

U.S. Appl. No. 18/819,429, filed Aug. 29, 2024, Denyer et al.

* cited by examiner

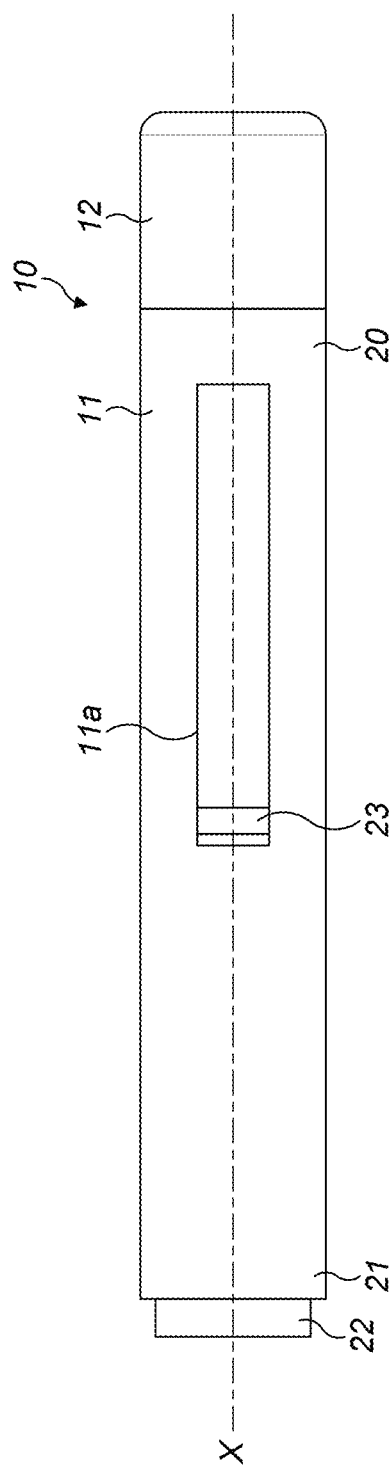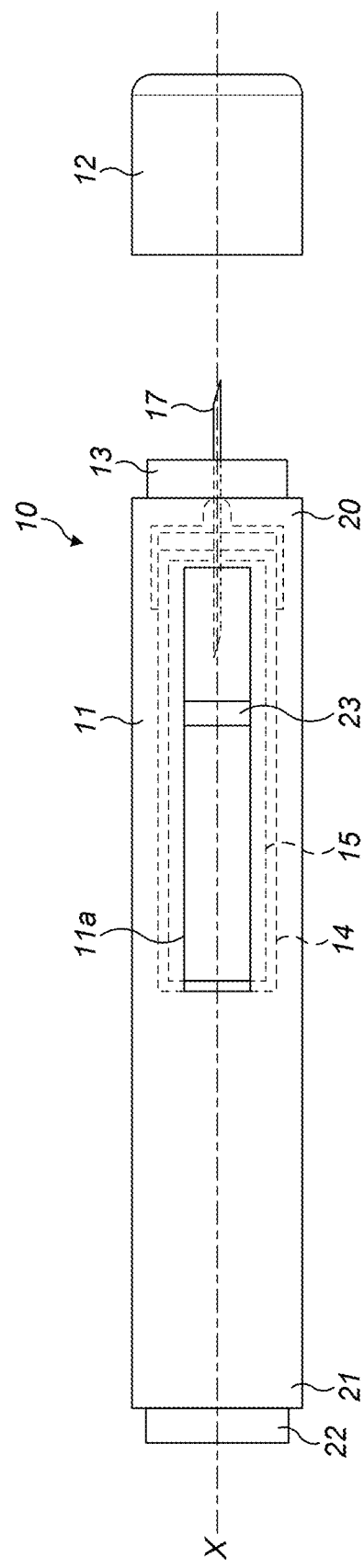

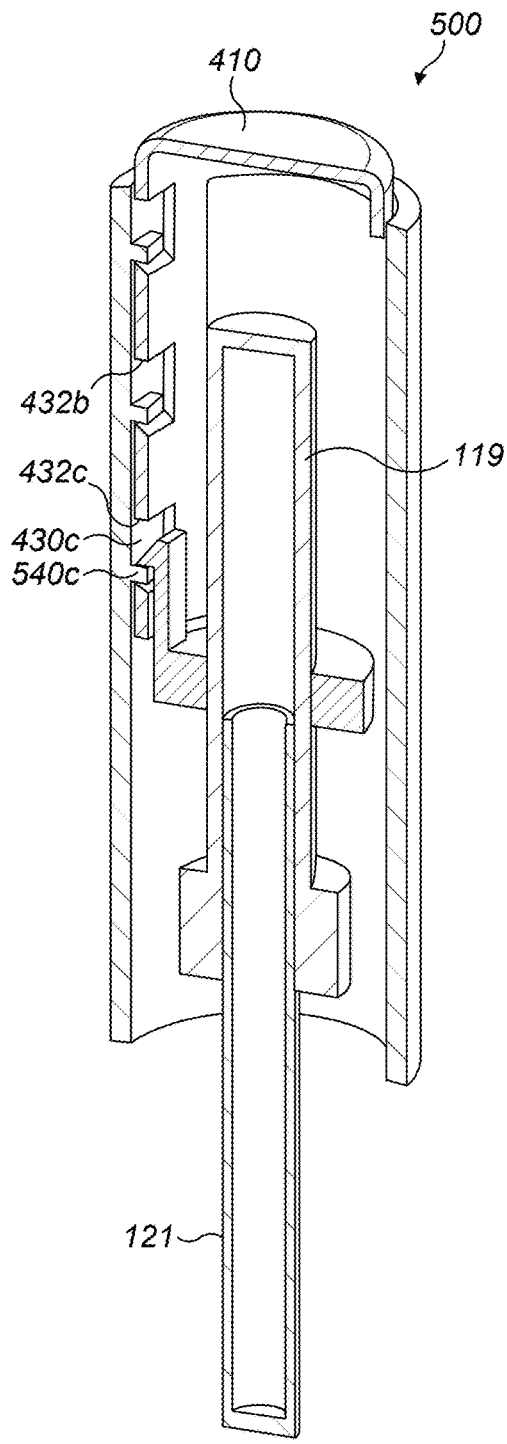
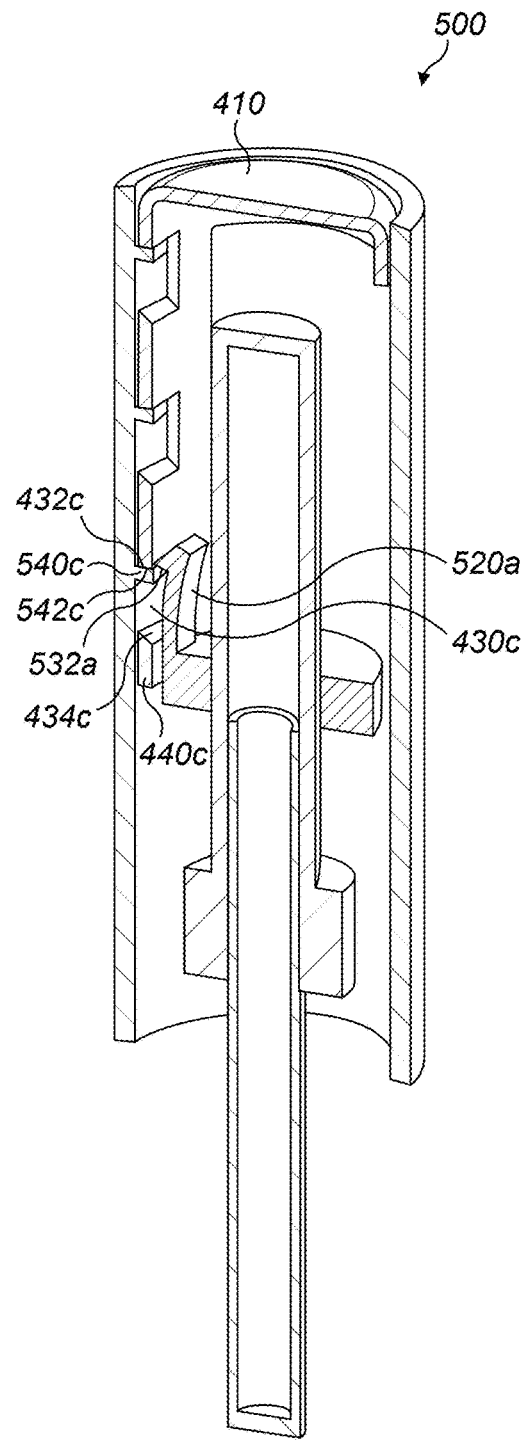
FIG. 5E
FIG. 5F

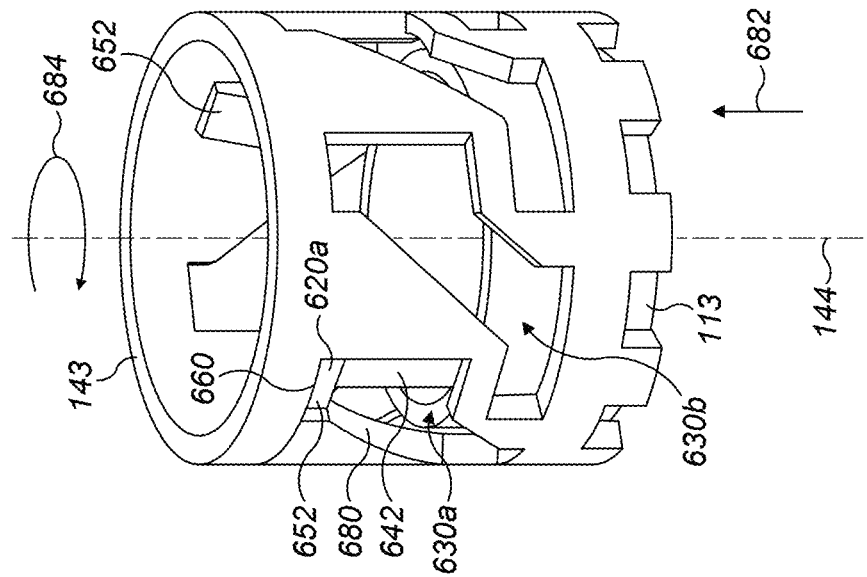
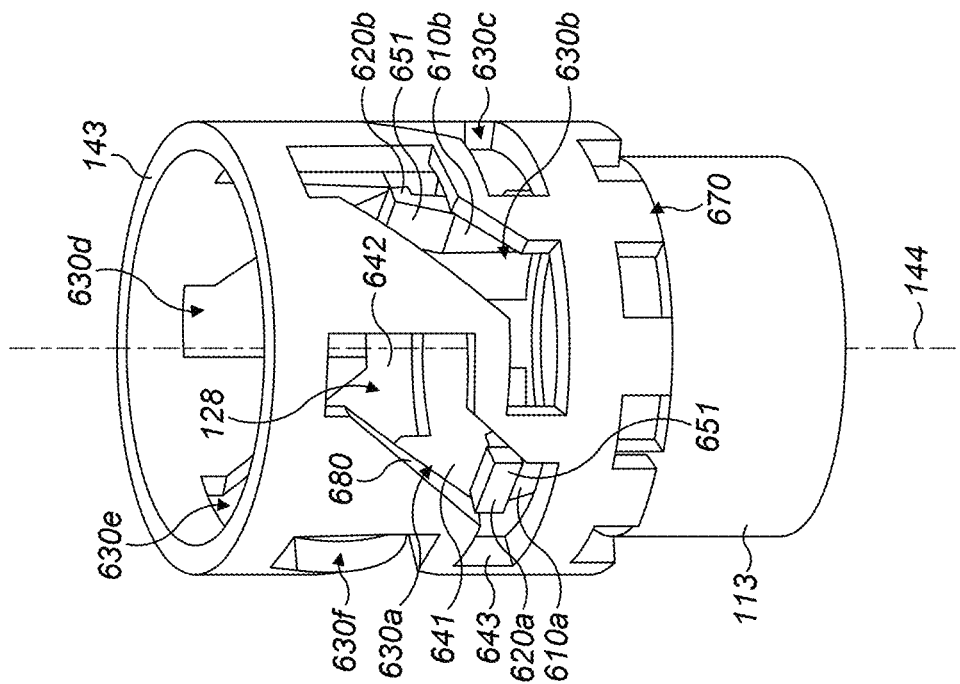
FIG. 6B
FIG. 6A

MEDICAMENT DELIVERY DEVICE

TECHNICAL FIELD

This application relates to a medicament delivery device for delivery of a medicament, a system comprising a medicament delivery device, and a method of using a medicament delivery device.

BACKGROUND

Drug delivery devices such as auto-injectors are used to deliver a range of medicaments. In an auto-injector device, some or all of the actions required to use the injector device in administering medicament are automated.

An auto-injector device may have a needle cover which is axially movable to cover and uncover a needle, with the needle cover being biased by a spring to extend over the needle. Typically, the user presses the needle cover against an injection site, against the force of the spring, to push the needle cover into the housing and to uncover the needle which is pushed into the injection site. Medicament is automatically dispensed from the needle via an automated mechanism. A user must typically hold the needle cover in a holding position for a predetermined period of time, to ensure that the correct dose of medicament is dispensed from the device, before removing the device from the injection site.

Some users may experience discomfort during the medicament delivery process. For example, some users may experience discomfort in the vicinity of the injection site when the delivered dose of medicament is large and/or delivered over a long period of time. If the discomfort becomes excessive, these users may decide to remove the auto-injector device from the injection site prematurely, which may result in incomplete delivery of the medicament dose, additional discomfort from premature withdrawal of the needle, and/or a wet injection site from leaked medicament.

The present disclosure provides an injector device that addresses one or more of the problems mentioned above, and to provide an improved injector device.

SUMMARY

A first aspect of this disclosure provides a medicament delivery device comprising: a body having a proximal end and a distal end, the body configured to hold a container containing a medicament; a needle cover axially movable relative to the body between an extended position and a retracted position; a medicament delivery mechanism comprising a plunger and a drive member, the drive member configured to move the plunger to dispense the medicament from the container; an actuation member configured to be actuated relative to the body; and a ratchet mechanism coupled to the medicament delivery mechanism and sequentially movable between a first configuration, a second configuration and a third configuration, wherein the actuation member and the ratchet mechanism are arranged such that: a first actuation of the actuation member moves the ratchet mechanism from the first configuration to the second configuration to cause a first dose of the medicament to be dispensed, and a second actuation of the actuation member, subsequent to the first actuation, moves the ratchet mechanism from the second configuration to the third configuration to cause a second dose of the medicament to be dispensed.

The actuation member may comprise a button arranged to be pushed a first time to provide the first actuation and pushed a second time to provide the second actuation.

The actuation member may be movable between a first position and a second position, wherein the first actuation of the actuation member comprises a first movement of the actuation member from the first position to the second position, and wherein the second actuation of the actuation member comprises a second movement of the actuation member from the first position to the second position, the second movement subsequent to the first movement.

The ratchet mechanism may comprise: a ratchet shuttle axially movable by the drive member and comprising a protrusion; and an engagement track comprising a first engagement element and a second engagement element, wherein the protrusion is configured to engage the first engagement element when the ratchet mechanism is in the first configuration, to limit axial movement of the ratchet shuttle by the drive member.

The protrusion may be configured to engage the second engagement element when the ratchet mechanism is in the second configuration, to limit axial movement of the ratchet shuttle by the drive member.

The arm may comprise a plurality of apertures and a plurality of guide surfaces arranged such that the apertures and guide surfaces alternate in an axial direction.

The ratchet shuttle may be a ratchet collar.

The actuation member and ratchet mechanism may be configured such that: the first actuation of the actuation member disengages the protrusion from the first engagement element to cause the protrusion to move axially to the second engagement element; and the second actuation of the actuation member disengages the protrusion from the second engagement element to cause the protrusion to move axially.

The medicament delivery device may further comprise a needle cover axially movable relative to the body between an extended position, in which a distal end of the needle cover is distal to a distal end of a needle, and a retracted position, in which the distal end of the needle is distal to the distal end of the needle cover.

The medicament delivery device may further comprise a needle cover biasing member configured to bias the needle cover distally.

The medicament delivery device may further comprise a needle cover guide having a track configured to be engaged by a guide protrusion of the needle cover such that an axial movement of the needle cover from the extended position to the retracted position causes a rotation of the needle cover guide relative to the needle cover.

The track may comprise a locking element arranged such that an axial movement of the needle cover from the retracted position to the extended position subsequent to the rotation of the needle cover guide engages the guide protrusion with the locking element, to limit a further axial movement of the needle cover from the extended position to the retracted position.

The medicament delivery device may be configured such that a further rotation of the needle cover guide relative to the needle cover disengages the guide protrusion from the locking element to allow the further axial movement of the needle cover from the extended position to the retracted position.

The medicament delivery device may be configured to be releasably coupled to a needle unit comprising a needle, wherein the needle cover guide is configured such that the further rotation is performed as the needle unit is coupled or uncoupled from the medicament delivery device by a needle unit tool releasably coupled to the needle cover guide.

The medicament delivery device of may further comprise an actuation member latch movable between a locked configuration, in which actuation of the actuation member is limited, and an unlocked configuration, in which actuation of the actuation member is allowed.

The actuation member latch may be configured to be moved from the locked configuration to the unlocked configuration by movement of the needle cover from the extended position to the retracted position.

The actuation member and the ratchet mechanism may be arranged such that: a third actuation of the actuation member moves the ratchet mechanism from the third configuration to a fourth configuration to cause a third dose of the medicament to be dispensed.

The medicament delivery device may further comprise the medicament.

A second aspect of this disclosure provides a system comprising: a medicament delivery device as disclosed herein; a needle unit releasably couplable to the medicament delivery device; and a needle unit tool for coupling the needle unit to the medicament delivery device or uncoupling the needle unit from the medicament delivery device.

A third aspect of this disclosure provides a method of operating a medicament delivery device as disclosed herein, the method comprising: actuating the actuation member of the medicament delivery device to dispense a first dose of the medicament; and subsequent to actuating the actuation member of the medicament delivery device to dispense the first dose of the medicament, actuating the actuation member of the medicament delivery device to dispense a second dose of medicament.

BRIEF DESCRIPTION OF THE DRAWINGS

Exemplary embodiments of the present disclosure are described with reference to the accompanying drawings, in which:

FIG. 1A shows an injector device with a cap attached;

FIG. 1B shows the injector device of FIG. 1A with the cap removed;

FIG. 5E is a cross-sectional perspective view of a portion of the medicament delivery device of FIG. 5D, after dispensing of the second dose of medicament, and prior to dispensing a third dose of medicament;

FIG. 5F is a cross-sectional perspective view of a portion of the medicament delivery device of FIG. 5E, during dispensing of the third dose of medicament;

FIG. 6A is a perspective view of a needle cover guide and portion of a needle cover of the medicament delivery device of FIG. 3A;

FIG. 6B is a perspective view of a needle cover guide and portion of a needle cover of the medicament delivery device of FIG. 3B;

DETAILED DESCRIPTION

Figure 2:
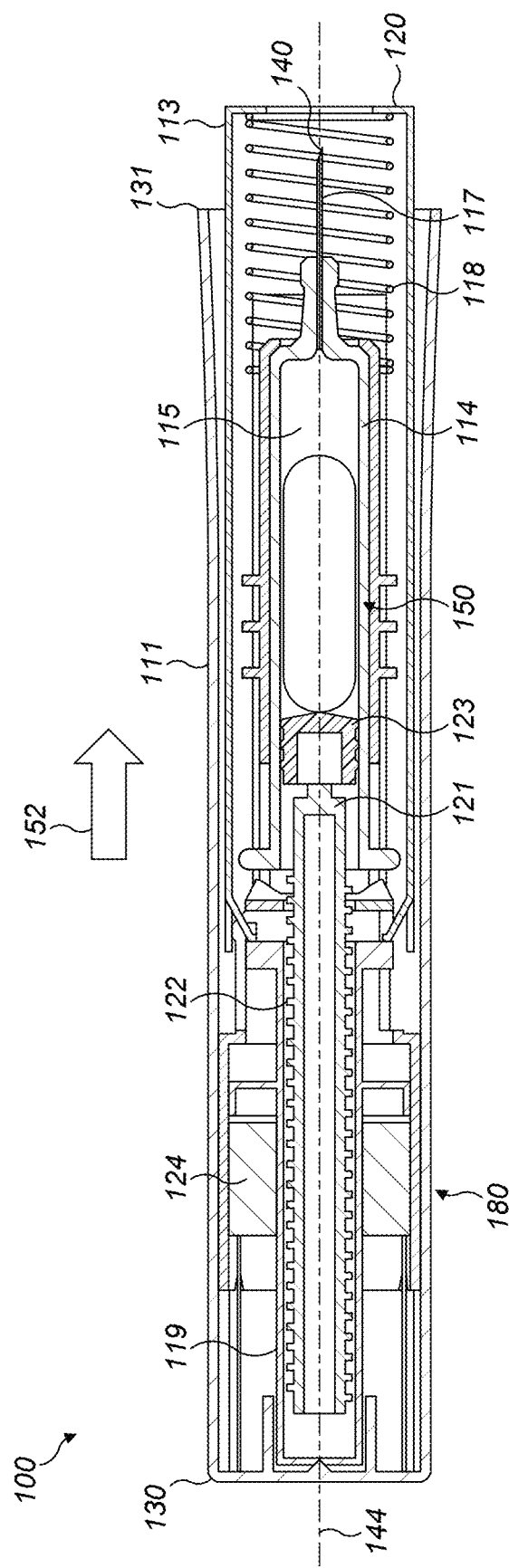
FIG. 2 is a cross-sectional view of a medicament delivery device.

One or more aspects of the present disclosure may provide a medicament delivery device configured to dispense a medicament in a plurality of discrete doses, a system comprising a medicament delivery device configured to dispense a medicament in a plurality of discrete doses, and a method of using a medicament delivery device configured to dispense a medicament in a plurality of discrete doses.

A drug delivery device (also referred to as a medicament delivery device), as described herein, may be configured to inject a medicament into a subject (e.g., a patient). For example, delivery could be sub-cutaneous, intra-muscular, or intravenous. Such a device could be operated by the subject themselves (i.e., 'self-administration') or by a different user, such as a nurse or physician providing care to the subject, and can include various types of safety syringe, pen-injector, or auto-injector. The device can include a cartridge-based system that requires piercing a sealed ampule before use. Volumes of medicament delivered with these various devices can range from about 0.5 ml to about 2 ml (e.g., to about 2.25 ml). Yet another device can include a large volume device ("LVD") or patch pump (in some instances referred to as an on body injector (OBI) or on body device (OBD)), configured to adhere to a subject's skin for a period of time (e.g., about 5, 15, 30, 60, or 120 minutes) to deliver a "large" volume of medicament (typically about 2 ml to about 10 ml, or about 2 mL to about 20 mL).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve (also referred to as a needle cover), or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle sleeve in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament 15 into a subject's body. Device 10 includes a housing 11, which may also be referred to as a body, which typically contains a reservoir 14 containing the medicament 15 to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated. Device 10 can include a window 11a through which a user may view medicament 15 remaining in the reservoir 14.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of the needle sleeve 13 relative to housing 11. For example, needle sleeve 13 can move in a longitudinal direction parallel to longitudinal axis X. Specifically, movement of needle sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of needle sleeve 13 by placing a distal end of sleeve 13 against a subject's body and moving housing 11 in a distal direction will uncover the distal end of the needle 17. Such relative movement allows the distal end of the needle 17 to extend into the injection site, such as a portion of the subject's body. Such insertion is termed "manual" insertion as needle 17 is manually inserted via the subject's manual movement of housing 11 relative to the needle sleeve 13.

Another form of insertion is "automated," whereby the needle 17 moves relative to housing 11. Such insertion can be triggered by movement of the needle sleeve 13 or by another form of activation, such as, for example, a button 22. As shown in FIGS. 1A & 1B, the button 22 is located at a proximal end of housing 11. However, in other embodiments, the button 22 could be located on a side of housing 11.

Other manual or automated features can include drug injection or needle retraction, or both. Injection is the process by which a bung or piston 23 is moved from a proximal location within a syringe (not shown in FIGS. 1A and 1B) to a more distal location within the syringe in order to force a medicament 15 from the syringe through needle 17. In some embodiments, a biasing member such as a drive spring (not shown in FIGS. 1A and 1B) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament 15 within the syringe, forcing it out of needle 17.

Following injection, needle 17 can be retracted within the needle sleeve 13 or housing 11. Retraction can occur when the needle sleeve 13 moves distally as a user removes device 10 from a subject's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 shows a simplified view of a medicament delivery device 100 that extends along an axis 144. The medicament delivery device 100 may share one or more features with the drug delivery device 10 discussed in relation to FIGS. 1A and 1B.

The medicament delivery device 100 may be configured to inject greater than 2 ml of medicament and/or the medicament delivery device 100 may be configured to inject medicament having a viscosity of greater than 25 cP. Nevertheless, in other examples the medicament delivery device 100 may be configured to inject 2 ml or less of medicament and/or the medicament delivery device 100 may be configured to inject medicament having a viscosity of 25 cP or less.

The medicament delivery device 100 has a body 111 having a proximal end 130 and a distal end 131 arranged along the axis 144, a hollow needle 117 for injecting medicament 115, and a needle cover 113. The body 111 is shown to be substantially cylindrical, however it should be understood that the body 111 may have a different shape in other examples.

The body 111 houses a pre-filled syringe 150, which comprises a container 114 containing the medicament 115. The needle 117 is coupled to a distal end of the container 114 and is in fluid communication with an interior of the container 114 such that the medicament 115 may be dispensed from the container 114, via the needle 117. FIG. 2 shows the needle 117 permanently coupled to the container 114, however it should be understood that this is not meant to be limiting. For example, in other instances, the needle 117 may be removably couplable to the container 114 (e.g., via a Luer lock interface between a connector on the container 114 and a connector coupled to the needle 117) such that the needle 117 may be coupled to the container 114 prior to an injection and uncoupled from the container 114 after an injection (e.g., to replace the needle 117 with a new needle 117).

The syringe 150 further comprises a bung or piston 123 arranged within the container 114, proximal to the medicament 115 and the needle 117. The piston 123 is arranged within the container 114 to be moved distally to force the medicament 115 out of the container 114, via the needle 117.

The needle 117 has a distal end 140. The needle cover 113 is proximally movable relative to the body 111 between an extended position, in which the needle cover 113 covers the distal end 140 of the needle 117, and a retracted position, in which the distal end 140 of the needle 117 protrudes from the needle cover 113 for penetration into an injection site. FIG. 2 shows the device 100 with the needle cover 113 in the extended position. The medicament delivery device 100 further comprises a needle cover biasing member 118, such as a spring, configured to bias the needle cover 113 axially in the distal direction. The distal direction is indicated by the direction of the arrow 152 in FIG. 2.

The medicament delivery device 100 comprises a medicament delivery mechanism 180 for dispensing the medicament 115 from the syringe 150 held within the body 111. The medicament delivery mechanism 180 comprises a plunger 121, a rotary collar 119 and a drive member 124.

The plunger 121, which may be coaxial with the axis 144, is axially movable within the syringe 150 of the device 100 in a distal direction to dispense the medicament 115 from the syringe 150 via the needle 117. The plunger 121 is arranged to engage the piston 123 of the syringe 150 such that distal axial movement of the plunger 121 moves the piston 123 distally to dispense the medicament 115 via the needle 117.

The rotary collar 119, which may also be coaxial with the axis 144, is axially fixed relative to the body 111 but is rotatable within the body 111 (e.g., about the axis 144). The drive member 124 is configured to rotate the rotary collar 119 when the drive member 124 is actuated/released. For example, the drive member 124 may be a spring (e.g., a torsion spring), wherein the spring is configured to rotate the rotary collar 119 when the spring is released. However, it should be understood that one or more other types of drive member 124 may be used instead, such as a pneumatic drive member. The drive member 124 is released when the needle cover 113 reaches a predetermined axial displacement with respect to the body 111.

The rotary collar 119 and the plunger 121 are arranged such that the rotation of the rotary collar 119 by the drive member 124 causes the plunger 121 to move distally within the syringe 150, to thereby dispense the medicament 115 from the syringe 150 via the needle 117. For example, the plunger 121 may comprise an external screw thread 122 that is configured to interface with an internal screw thread of the rotary collar 119 such that rotation of the rotary collar 119 causes distal translation of the plunger 121. However, it should be understood that other forms of interface between the rotary collar 119 and the plunger 121 for converting rotation of the rotary collar 119 into translation of the plunger 121 may be used instead. For example, in other instances, only one of the rotary collar 119 and the plunger 121 may have a screw thread, and the other of the rotary collar 119 and the plunger 121 may have one or more engagement features, such as one or more projections, that are arranged to engage with the screw thread such that rotation of the rotary collar 119 causes translation of the plunger 121.

To initiate delivery of the medicament 115 into a subject (who may be the user of the medicament delivery device 100, a different person to the user of the device, or an non-human animal), a distal end 120 of the needle cover 113 is to be pressed against the injection site on the subject and the body 111 is moved towards the injection site, thereby moving the needle cover 113 axially into the body 111 and uncovering the needle 117 from within the needle cover 113 such that it penetrates the injection site. The proximal axial displacement of the needle cover 113 causes the release of the drive member 124, which rotates the rotary collar 119. The rotation of the rotary collar 119 moves the plunger 121 axially within the syringe 150 to dispense the medicament 115 into the injection site via the needle 117. The device 100 is pressed against the injection site to hold the needle cover 113 in its retracted position whilst the medicament 115 is dispensed from the device 100.

After the medicament 115 has been dispensed, the device 100 is removed from the injection site by moving the body 111 away from the injection site. In doing so, the needle cover 113 moves distally under the force of the biasing member 118 towards the extended position to cover the distal end 140 of the needle 117 and therefore protect the user and/or subject from an accidental needle-stick event. In some instances, subsequent proximal movement of the needle cover 113 relative to the body 111 may be inhibited by a locking mechanism.

FIGS. 3A to 3K show a schematic cross-section view of a medicament delivery device 200 (which may be an autoinjector) in various stages of operation, in accordance with one or more aspects of the present disclosure.

The features described and/or contemplated in relation to the medicament delivery device 200 may be incorporated in the medicament delivery device 100 described and/or contemplated above in relation to FIG. 2. Alternatively, or additionally, the features described and/or contemplated in relation to the medicament delivery device 200 may be incorporated in another medicament delivery device, for example a medicament delivery device having a different mechanism for dispensing a medicament to that described in relation to the medicament delivery device 100. Like references refer to like features.

Figure 3A:
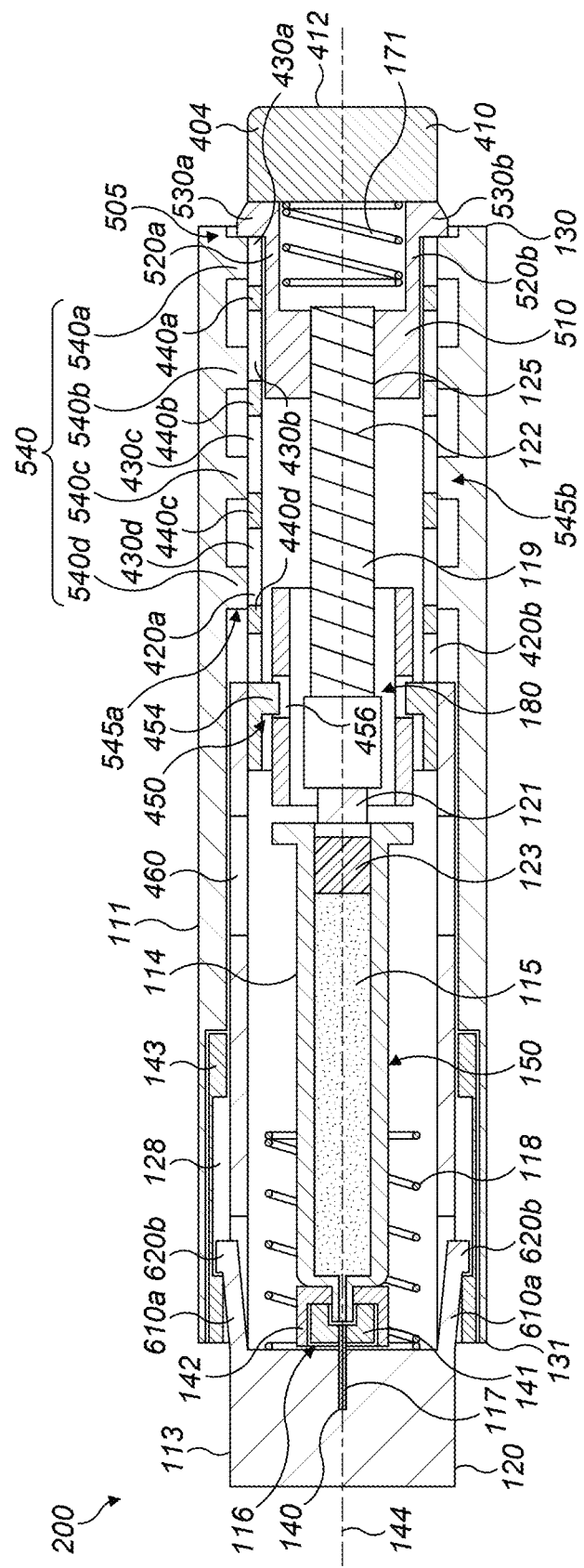
FIG. 3A is a schematic cross-sectional view of a medicament delivery device in accordance with one or more embodiments, in a first state.

With reference to FIG. 3A, the medicament delivery device 200 includes a body 111, also referred to as a housing, extending along an axis 144 of the medicament delivery device 200 and having a proximal end 130 and a distal end 131. The body 111 is substantially cylindrical, however this is not meant to be limiting, and it should be understood that other shapes may be envisaged for the body 111 that are not cylindrical. A syringe 150 comprising a container 114 containing a medicament 115 is held within the body 111.

The medicament delivery device 200 includes a needle unit 116 that is releasably couplable to the syringe 150 such that it can be coupled to the syringe 150 and uncoupled from the syringe 150 by a user. The needle unit 116 comprises a hollow needle 117 for injecting the medicament 115 and a connection interface 141 configured to releasably couple to a corresponding connection interface 142 of the syringe 150. When the needle unit 116 is coupled to syringe 150, the needle 117 is in fluid communication with the container 114 such that medicament 115 may be dispensed from the container 114 via the needle 117.

In some examples, a distal end of the container 114 may be sealed by a septum that is configured to be pierced by a proximal end of the needle 117 (or a different needle of the needle unit 116 that is in fluid communication with the needle 117) to bring the needle 117 into fluid communication with the medicament 115 within the container 114. However, it should be noted that in other examples, no pierceable septum is used (e.g., since the medicament 115 is prevented from leaving the container 114 prior to connection of the needle unit 116 by surface tension of the medicament 115 and/or pressure differentials).

Various alternative mechanisms for connecting the needle unit 116 and the syringe 150 may be employed. For example, in some examples, the connection interface 141 and connection interface 142 may be configured to provide a screw connection, wherein the needle unit 116 is configured to be screwed onto the connection interface 142 to couple the needle unit 116 to the syringe 150 and/or wherein the needle unit 116 is configured to be unscrewed from the connection interface 142 to uncouple the needle unit 116 from the syringe 150. To screw the needle unit 116 onto the connection interface 142, the screw-type connection interface 141 of the needle 116 is brought into engagement with the screw-type connection interface 142 of the syringe 150 by simultaneous rotation (e.g., about axis 144) and proximal translation of the needle unit 116 relative to the medicament delivery device 200 (e.g., relative to the syringe 150). To unscrew the needle unit 116 from the connection interface 142, the screw-type connection interface 141 of the needle 116 is brought out of engagement with the screw-type connection interface 142 of the syringe 150 by rotation of the needle unit 116 in an opposite direction to the direction used to couple the needle unit 116 and the syringe 150, simultaneous with distal translation of the needle unit 116 relative to the medicament delivery device 200 (e.g., relative to the syringe 150). As an example, of a screw-type connection, the connection interface 141 and connection interface 142 may provide a Luer lock connection when coupled, with the connection interface 141 comprising one of a male or female Luer lock connector and the connection interface 142 comprising the other of a male or female Luer lock connector.

In additional or alternative examples, the needle unit 116 may be configured to be coupled and/or uncoupled from the syringe 150 using a snap-fit connection. For example, to couple the needle unit 116 to the connection interface 142, a snap-fit connection interface 141 of the needle unit 116 may be moved axially relative to the medicament delivery device 200 and syringe 150, in the proximal direction, until the snap-fit connection interface 141 of the needle unit 116 engages a snap-fit connection interface 142 of the syringe 150. The relative axial movement is continued until the snap-fit connection between the connection interface 141 of the needle unit and the connection interface 142 of the syringe 150 is formed, at which point the needle unit 116 is coupled to the syringe 150. To uncouple the needle unit 116 from the connection interface 142, a snap-fit connection interface 141 of the needle unit may be moved axially relative to the medicament delivery device 200 and syringe 150, in the distal direction, until a coupling force between the snap-fit connection interface 141 of the needle unit 116 and the snap-fit connection interface 142 is overcome, separating the needle unit 116 from the syringe 150.

It should be noted that in some examples, the needle unit 116 may be configured to couple to the syringe connection interface 142 using a different mechanism to the mechanism used for uncoupling the needle unit 116 from the syringe connection interface 142. For example, in some examples the connection interface 141 of the needle unit 116 and the connection interface 142 of the syringe 150 may be configured to be coupled together by a snap-fit connection (e.g. by axially bringing the connection interfaces 141, 142 together, in some cases without relative rotation), but uncoupled by unscrewing the connection interface 141 from the connection interface 142. In other examples, the connection interface 141 of the needle unit 116 and the connection interface 142 of the syringe 150 may be configured to be coupled together by a screwing the connection interfaces 141, 142 together, but uncoupled by axially separating the connection interface 141 from the connection interface 142 (e.g., as described in relation to the snap-fit connection, in some examples without relative rotation between the connection interfaces 141, 142).

Additionally or alternatively, other types of connection between the connection interfaces 141, 142 may be employed such as a bayonet connection (in which the relative axial and then rotational movement is used to connect the connection interfaces 141, 142, and then relative rotational and then axial movements in the opposite directions are used to uncouple the connection interfaces 141, 142), or a friction-fit connection (e.g., a Luer slip connection) which employs relative axial movement to couple and/or uncouple the connection interfaces 141, 142 (optionally in combination with relative rotation). Again, in some examples, a different mechanism for coupling the connection interfaces 141, 142 compared to uncoupling the connection interfaces 141, 142 may be used (e.g., the connection interfaces 141, 142 may be coupled by a snap-fit connection but uncoupled by a bayonet connection).

The various types of connections and/or combinations of connection types disclosed herein are not meant to be limiting, and it should be envisaged that other types of connections and/or combinations of connection types may be employed with aspects of the present disclosure.

The needle unit 116 can be uncoupled from the medicament delivery device 200 and replaced by another needle unit 116 between injections, for example using one or more needle unit tools, as described later.

As shown in FIG. 3A, the medicament delivery device 200 includes a needle cover 113 axially movable relative to the body 111 between an extended position and a retracted position. When the needle cover 113 is in the extended position and the needle unit 116 is coupled to the medicament delivery device 200, the needle cover 113 extends from the distal end 131 of the body 111 such that a distal end 140 of the needle 117 is surrounded, to protect a user from an accidental needle-stick injury prior to an actual injection. When the needle cover 113 is in the retracted position and the needle unit 116 is coupled to the medicament delivery device 200, the distal end 140 of the needle 117 protrudes distally from the distal end 120 of the needle cover 113 such that the distal end 140 of the needle 117 can penetrate an injection site.

A needle cover biasing member 118, which in this example takes the form of a spring, is configured to bias the needle cover 113 distally, from the retracted position to the extended position. It should be understood that in other examples the needle cover biasing member 118 may take a different form to a spring, for example a pneumatic mechanism or an elastic polymer.

In FIG. 3A, the medicament delivery device 200 is shown in a first state prior to an injection, in which the medicament delivery device 200 is not being held against an injection site. The needle cover 113 is in the extended position with respect to the body 111, biased into the extended position by the needle cover biasing member 118. The needle cover 113 is axially movable relative to the body 111 between the extended position shown in FIG. 3A, in which a distal end 120 of the needle cover 113 is distal to a distal end 140 of the needle 117, and the retracted position shown in FIG. 3B, in which the distal end 140 of the needle 117 is distal to the distal end 120 of the needle cover 113.

The medicament delivery device 200 comprises a medicament delivery mechanism 180 for dispensing the medicament 115 from the syringe 150 held within the body 111. The medicament delivery mechanism 180 in this example comprises a plunger 121, a rotary collar 119 and a drive member such as a spring (e.g., torsion spring), one or more of which may be as described above in relation to the device 100. However, it should be understood that in other examples, the medicament delivery mechanism 180 may comprise one or more different components than a plunger 121, a rotary collar 119 and/or drive member. The drive member is hidden in FIGS. 3A-3K, but may be arranged to at least partially surround the rotary collar 119.

The plunger 121, which may be coaxial with the axis 144, is axially movable within the syringe 150 of the medicament delivery device 200 to dispense medicament 115 from the syringe 150 via the needle 117. The plunger 121 is located proximal to a piston 123 of the syringe 150. FIG. 3A shows that the distal end of the plunger 121 is initially axially separated from the piston 123 when the medicament delivery device 200 is in its first state. However, it should be understood that in other examples the distal end of the plunger 121 may be engaged with the piston 123 when the medicament delivery device 200 is in its first state.

The rotary collar 119, which may be coaxial with the axis 144, is axially fixed relative to the body 111 but is able to rotate with respect to the body 111 (e.g., about the axis 144). The drive member is configured to rotate the rotary collar 119 when released, to move the plunger 121 to dispense the medicament 115 from the container 114. The drive member may be a spring such as a torsion spring, however other forms of spring/drive member may be used instead.

The rotary collar 119 interfaces with the plunger 121 (e.g. via any of the interfaces previously described in relation to FIG. 2, such as an internal screw thread 125 of the rotary collar 119 interfacing with an external screw thread 122 of the plunger 121) such that the rotation of the rotary collar 119 by the drive member causes the plunger 121 to move distally within the syringe 150 to thereby dispense medicament 115 from the syringe 150 via the needle 117 (e.g., in the same or similar manner as previously described in relation to FIG. 2).

The medicament delivery device 200 further comprises an actuation member 404, an actuation member latch 450, and a ratchet mechanism 505. Aspects of the actuation member 404 and the ratchet mechanism 505 are also described in relation to FIGS. 5A-5G, which are schematic cross-sections of a proximal end of a medicament delivery device 500, which may share one or more features of the medicament delivery device 200 described in relation to FIGS. 3A-3K. Some features of the medicament delivery 200 device shown in FIGS. 3A-3K such as the spring 171 and the actuation member latch 450 are hidden in FIGS. 5A-5G for clarity.

The ratchet mechanism 505 is coupled to the medicament delivery mechanism 180 and is configured for causing the medicament delivery mechanism 180 to dispense the medicament 115 in a plurality of discrete, predefined doses. The ratchet mechanism 505 is configured to be sequentially moved between a plurality of configurations, wherein movement of the ratchet mechanism 505 between each configuration causes the medicament delivery mechanism 180 to dispense a respective dose of medicament 115 of the plurality of doses. The ratchet mechanism 505 comprises at least a first configuration, a second configuration and a third configuration, wherein movement of the ratchet mechanism 505 from the first configuration to the second configuration causes a first dose of the medicament 115 to be dispensed, and wherein subsequent movement of the ratchet mechanism 505 from the second configuration to the third configuration causes a second dose of the medicament 115 to be dispensed. If the ratchet mechanism 505 comprises a fourth configuration, then subsequent movement of the ratchet mechanism 505 from the third configuration to the fourth configuration may cause a third dose of the medicament 115 to be dispensed (with subsequent movement to a fifth configuration, if present, causing a fourth dose to be dispensed etc.).

Figure 5A:
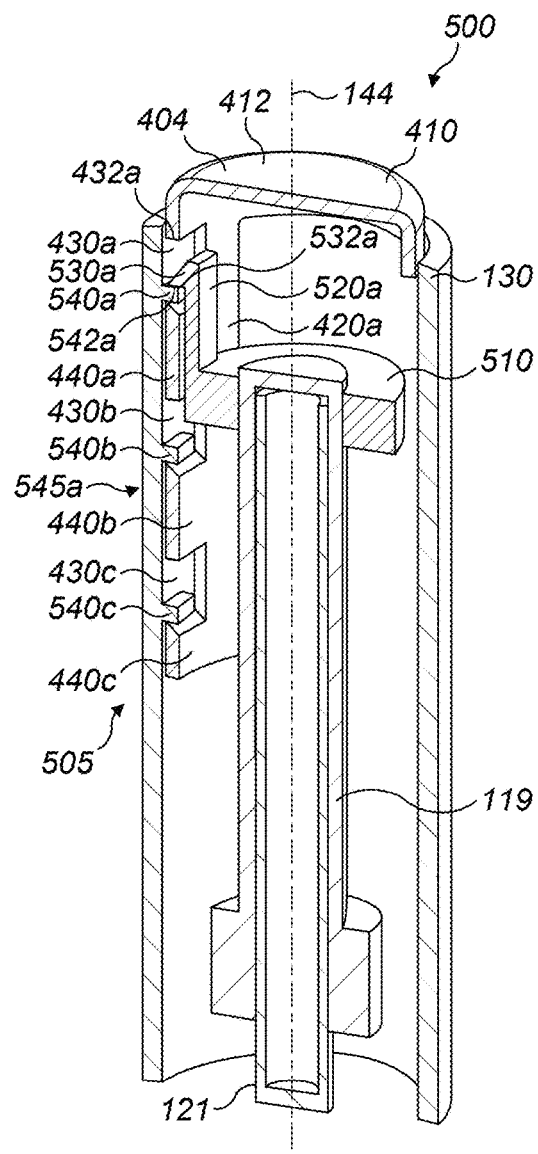
FIG. 5A is a cross-sectional perspective view of a portion of a medicament delivery device in accordance with one or more embodiments, prior to dispensing a first dose of medicament.

As shown in FIG. 3A and FIG. 5A, the ratchet mechanism 505 comprises a plurality of engagement elements 540 and an axially movable ratchet shuttle, in this example the ratchet shuttle being in the form of a ratchet collar 510.

The ratchet collar 510 is arranged within the body 111 to at least partially surround and engage the rotary collar 119. The ratchet collar 510 may be configured to move axially within respect to the body 111 and the rotary collar 119, but may be inhibiting from rotating relative to the body 111 and rotary collar 119, for example due to interaction with an axial guide (not shown). An interface between the ratchet collar 510 and the rotary collar 119 (e.g. a screw thread interface, similar to a screw thread interface previously described in relation to FIG. 2) is configured such that rotation of the rotary collar 119 (e.g., by the drive member) relative to the body 111 and the ratchet collar 510 causes the ratchet collar 510 to move axially relative to the rotary collar 119 and the body 111. The axial movement of the ratchet collar 510 may be brought about at least in part by the axial guide limiting rotation of the ratchet collar 510 relative to the body 111. FIG. 3A shows the ratchet collar 510 in a first axial position relative to the body 111. Rotation of the rotary collar 119 for medicament delivery causes the ratchet collar 510 to move axially along the axis 144 in the distal direction, as shown in the progression of FIGS. 3A to 3K.

The ratchet collar 510 comprises a pair of flexible arms 520a, 520b which extend in a proximal direction from a proximal surface of the main body of the ratchet collar 510, adjacent to the inner surface of the body 111, to each progressively engage the respective engagement elements 540 (e.g., respective engagement elements 540a, 540b, 540c, 540d). Each flexible arm 520a, 520b has a respective protrusion 530a, 530b that extends radially outwards from a free end of that flexible arm 520a, 520b such that the flexible arm 520a, 520b can engage the engagement elements 540 via the respective protrusion 530a, 530b. FIG. 3A show the protrusions 530a, 530b arranged at a proximal end of each flexible arm 520a, 520b. However, it should be understood that in other examples the protrusions 530a, 530b may be located at a different portion of the flexible arms 520a, 520b, for example distal to the proximal end of the flexible arms 520a, 520b. The pair of flexible arms 520a, 520b may be located at symmetrical positions of the ratchet collar 510 about the axis 144, as shown in FIG. 3A, or at different locations around the axis 144.

In FIG. 5A, only one flexible arm 520a and its corresponding protrusion 530a are shown, while the other flexible arm 520b and its corresponding protrusion 530b shown in FIG. 3A are hidden in FIG. 5A. However, it should be noted that in some alternative examples, the ratchet collar 510 comprises a single flexible arm 520a and corresponding protrusion 530a (i.e., flexible arm 520b is not present). In yet other examples, the ratchet collar 510 may comprise three flexible arms 520 and corresponding protrusions 530, or a number of flexible arms 520 and corresponding protrusions 530 that is greater than three.

The plurality of engagement elements 540 are shown in FIGS. 3A and 5A to be arranged along an inner surface of the body 111, however it should be understood that in other examples the engagement elements 540 are arranged along a different portion of the medicament delivery device 200 to the body 111, but are fixed relative to the body 111. The engagement elements 540 are configured to be engaged by the protrusion(s) 530 to limit axial movement of the ratchet collar 510 by the drive member.

Each engagement element 540 may take the form of a projection such as a ridge. The engagement elements 540 are grouped into sets of engagement elements 540, each set of engagement elements 540 forming a respective engagement track 545. The number of engagement tracks 545 may correspond to the number of flexible arms 520 (e.g., each flexible arm 520 has a respective engagement track 545). In FIG. 3A, two flexible arms 520a, 520b are shown, each having a respective engagement track 545a, 545b, and each engagement track 545a, 545b comprising a plurality of respective engagement elements 540a-540d. In alternative examples where the ratchet collar 510 comprises a single arm 520, the ratchet mechanism 505 may comprise a single engagement track 545 comprising a plurality of engagement elements 540.

For each engagement track 545a, 545b, the engagement elements 540 of that engagement track 545a, 545b are aligned along the inner surface of the body 111, along a respective axis that is substantially parallel to the axis 144. As such, each engagement track 545a, 545b extends axially along the inner circumferential surface of the body 111, parallel to the axis 144. Where a plurality of engagement tracks 545a, 545b are present, the engagement tracks 545a, 545b are arranged circumferentially around the inner circumferential surface of the body 111, with each engagement track 545a, 545b parallel to, but circumferentially separated from, its adjacent engagement track(s) 545a, 545b. FIG. 3A shows two engagement tracks 545a, 545b, each separated by 180 degrees about the axis 144 such that they are symmetrical about the axis 144. Each engagement track 545a, 545b is located adjacent its corresponding flexible arm 520a, 520b.

In FIG. 5A, only one of the engagement tracks 545a is shown, while the other engagement track 545b shown in FIG. 3A is hidden in FIG. 5A. However, it should be noted that in some alternative examples the ratchet mechanism 505 comprises a single engagement track 545 (e.g., where the ratchet collar 510 comprises a single flexible arm 520). In yet other examples, the ratchet mechanism 505 may comprise three or more engagement tracks 545 spaced around the body 111 (e.g., where the ratchet collar 510 comprises three or more flexible arms 520).

It should be noted that FIG. 3A shows the medicament delivery device 200 comprising four engagement elements 540a-540d per engagement track 545a, 545b, whereas FIG. 5A shows only three engagement elements 540a-c. The fourth engagement element 540d may be hidden in FIG. 5A, or it may not be present.

Each engagement track 545a, 545b may comprise the same number of engagement elements 540, wherein the number of engagement elements 540 in each engagement track 545 may correspond to the number of discrete doses of the medicament 115 that may be dispensed by the medicament delivery device 200, as explained later.

In examples where the medicament delivery device 200 is configured to dispense at least two discrete doses of medicament 115, each engagement track 545 may comprise at least two engagement elements 540a, 540b. In examples where the medicament delivery device 200 is configured to dispense at least three discrete doses of medicament 115, each engagement track 545 may comprise at least three engagement elements 540a, 540b, 540c. In examples where the medicament delivery device 200 is configured to dispense at least n (e.g., n=1, 2, 3, . . . ) discrete doses of medicament 115, each engagement track 545 may comprise at least n engagement elements 540.

Adjacent engagement elements 540 are separated by a distance in the direction of the axis 144 that corresponds to a predetermined size of a respective dose of medicament 115 to be dispensed. Each engagement element 540 of each engagement track 545 may be located at the same axial position with respect to the axis 144 as an engagement element 540 of the other engagement track(s) 545. For example, FIG. 3A shows a first engagement element 540a of the first engagement track 545a is located at the same axial position with respect to the axis 144 as a first engagement element 540a of the second engagement track 545b (i.e., they lie in the same plane normal to the axis 144). Similarly, a second engagement element 540b of the first engagement track 545a is located at the same axial position with respect to the axis 144 as a second engagement element 540b of the second engagement track 545b, a third engagement element 540c of the first engagement track 545a is located at the same axial position with respect to the axis 144 as a third engagement element 540c of the second engagement track 545b, and a fourth engagement element 540d of the first engagement track 545a is located at the same axial position with respect to the axis 144 as a fourth engagement element 540d of the second engagement track 545b.

The protrusion 530a, 530b of each flexible arm 520a, 520b of the ratchet collar 510 is configured to sequentially engage with each engagement element 540 in a corresponding engagement track 545a, 545b during a medicament delivery process, such that the medicament 115 can be delivered in the plurality of discrete, predefined doses, as described in more detail later.

As shown in FIGS. 3A and 5A, the actuation member 404 comprises a button 410 arranged at a proximal end of the medicament delivery device 200 to extend proximal to the proximal end 130 of the body 111 and having a proximal actuation surface 412 configured to be pushed by a user.

The actuation member 404 is configured to be actuated relative to the body 111. The actuation member 404 is actuatable by a user between a first axial position and a second axial position relative to the body 111. Each actuation of the actuation member 404 comprises a movement of the actuation member 404 between the first axial position and the second axial position.

Figure 3B:
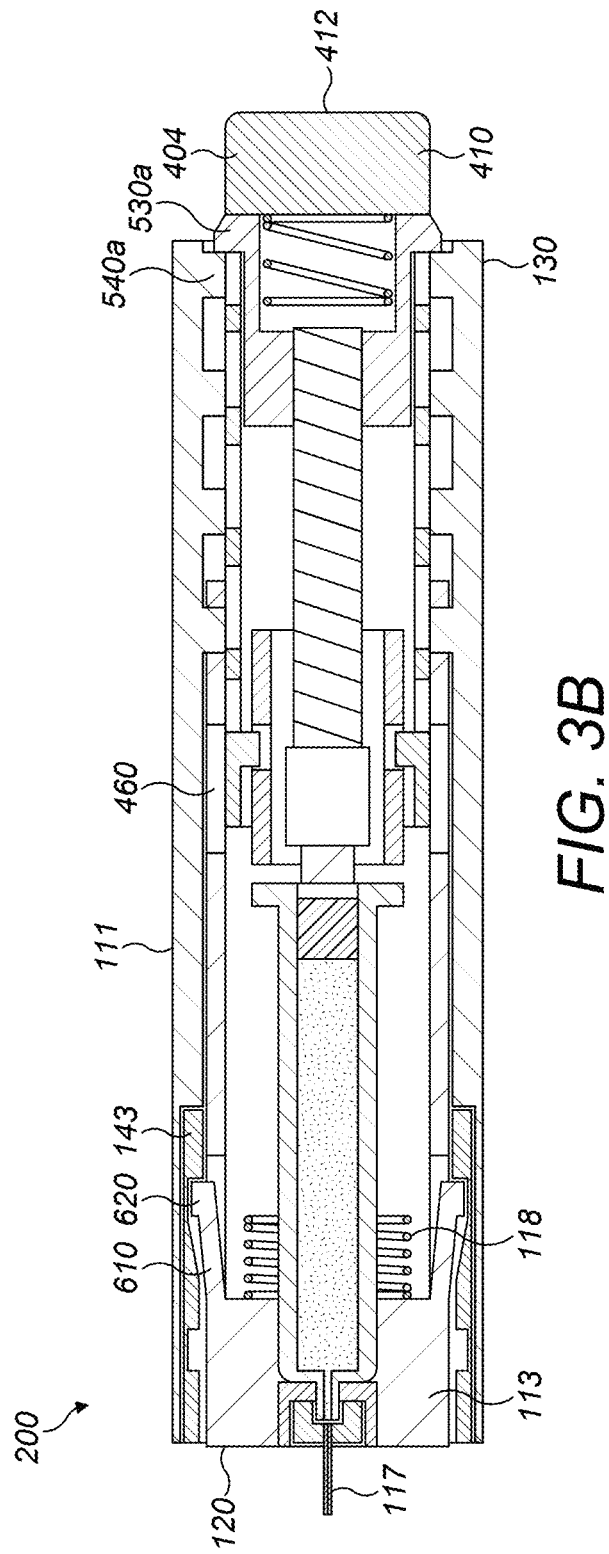
FIG. 3B is a schematic cross-sectional view of the medicament delivery device of FIG. 3A, in a second state.
Figure 3C:
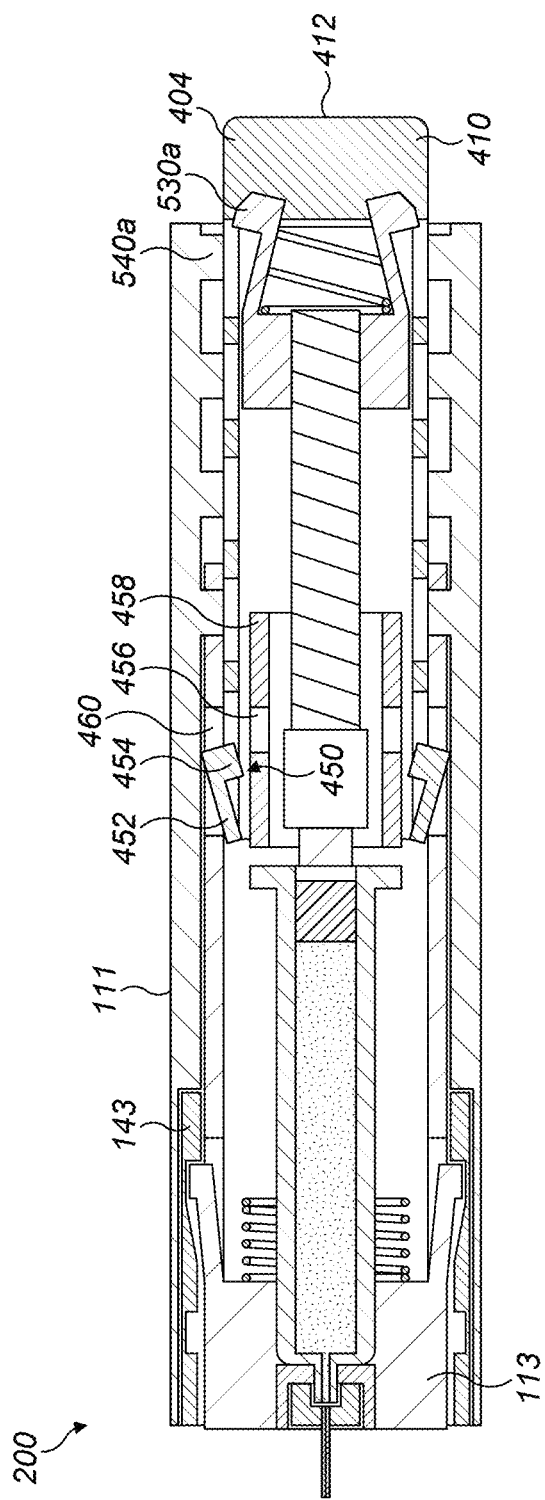
FIG. 3C is a schematic cross-sectional view of the medicament delivery device of FIG. 3B, in a third state.

FIG. 3A shows the actuation member 404 in the first axial position relative to the body 111, while FIG. 3C shows the actuation member 404 in the second axial position relative to the body 111, the actuation member 404 having been moved distally from the first axial position to the second axial position by actuation (e.g., movement in the distal direction) of the actuation member 404 by a user. A user may apply a distal axial force to the actuation member 404 by directly pressing the proximal actuation surface 412 of the actuation member 404 with a thumb or finger to move the actuation member 404 distally between the first axial position and the second axial position. The button 410 is arranged to be pushed a first time by the user to provide a first actuation and pushed a second time by the (or a different) user to provide a second actuation (and pushed a third time by the user to provide a third actuation etc.).

The actuation member 404 may be biased from its second axial position to its first axial position by an actuation member biasing member such as a spring 171, however other forms of actuation member biasing member to a spring 171 may be envisaged.

The actuation member 404 and the ratchet mechanism 505 are arranged such that actuation of the actuation member 404 (e.g., movement of the actuation member 404 from its first axial position to its second axial position) can be used move the ratchet mechanism 505 between configurations to dispense a dose of medicament 115, as described later in relation to FIGS. 5A-5G. For example, a first actuation of the actuation member 404 moves the ratchet mechanism 505 from the first configuration to the second configuration to cause a first dose of the medicament 115 to be dispensed, and a second actuation of the actuation member 404, subsequent to the first actuation, moves the ratchet mechanism 505 from the second configuration to the third configuration to cause a second dose of the medicament 115 to be dispensed. Subsequent actuations of the actuation member 404 may be used to dispense subsequent discrete doses of medicament 115.

The actuation member 404 comprises a pair of elongate arms 420a, 420b that extend substantially in a distal direction from a distal end of the button 410, substantially parallel to the axis 144 and within the body 111. Each arm 420 extends adjacent the inner circumferential surface of the body 111, substantially parallel to said surface. The two arms 420a, 420b are arranged symmetrically either side of the axis 144.

Each arm 420a, 420b has a plurality of apertures 430 (e.g., apertures 430a, 430b, 430c, 430d), wherein the plurality of apertures 430 on each arm 420a, 420b are arranged along an axis that is substantially parallel to the axis 144. Each arm 420 further comprises a plurality of guide surfaces 440 (e.g., guide surfaces 440a, 440b, 440c, 440d), arranged such that the apertures 430 and guide surfaces 440 alternate in an axial direction, with each pair of adjacent apertures 430 having a guide surface 440 between. Each of the apertures 430 extend in a radial direction through their respective arm 420, from an inner surface of their respective arm 420 (nearest the axis 144) to an outer surface of their respective arm 420 (furthest from the axis 144). Each engagement element 540 is axially aligned with a corresponding aperture 440.

Operation of the ratchet mechanism 505 for dispensing the medicament 115 in a plurality of discrete doses shall now be described with particular reference to FIGS. 5A-5G.

FIG. 5A shows the proximal end of the medicament delivery device 500 (which may be identical or similar to the medicament delivery device 200) prior to medicament delivery.

The medicament delivery device 500 may have been positioned at an injection site of a subject (who may be the user of the device 500, or a different person/animal). The needle cover 113 may have been moved from its extended position to its retracted position as the medicament delivery device 500 was positioned at the injection site.

FIG. 5A shows the ratchet mechanism 505 in its first configuration. The actuation member 404 is at its first axial position relative to the body 111, and may be biased into this position by the spring 171. The rotary collar 119 is biased to rotate by the drive member, but is inhibited from rotation relative to the body 111 by the ratchet mechanism 505. More specifically, the protrusion 530a of the flexible arm 520a of the ratchet collar 510 is engaged with the first engagement element 540a of the first engagement track 545a (e.g., by engagement between a distal-facing engaging surface 532a of the protrusion 530a and a proximal-facing engaging surface 542a of the first engagement element 540a), such that axial movement of the ratchet collar 510 in the distal direction is limited (e.g., prevented).

Since the ratchet collar 510 is prevented from moving distally relative to the body 111, the interface between the ratchet collar 510 and the rotary collar 119 limits (e.g., prevents) rotation of the rotary collar 119 by the drive member, which in turn limits (e.g., prevents) axial movement of the plunger 121 in the distal direction relative to the body 111 due to the interface between the rotary collar 119 and the plunger 121. As such, the medicament delivery mechanism 180 does not operate to dispense the medicament while the ratchet collar 510 is engaged with the first engagement element 540a.

Figure 5B:
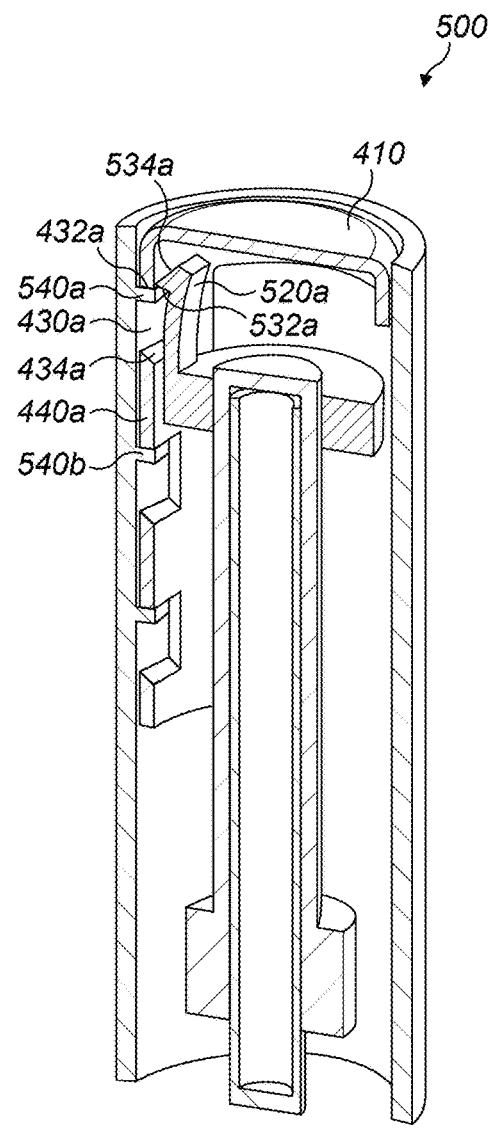
FIG. 5B is a cross-sectional perspective view of a portion of the medicament delivery device of FIG. 5A, during initiation of the dispensing of the first dose of medicament.

FIG. 5B shows the medicament delivery device 500 of FIG. 5A after delivery of a first dose of the medicament 115 has been initiated, by a first actuation of the actuation member 404. For example, a user may have applied a force to the proximal actuation surface 412 of the button 410 in a distal direction using a finger or thumb, moving the actuation member 404 distally from its first axial position shown in FIG. 5A to its second axial position shown in FIG. 5B.

The distal movement of the actuation member 404 to its second axial position causes the arm 420 of the actuation member 404 to disengage the protrusion 530a from the first engagement element 540a. As shown from FIG. 5A to FIG. 5B, the arm 420a engages the protrusion 530a of the flexible arm 520a such that the flexible arm 520a is flexed radially inwards as the arm 420a moves distally. More specifically, a distal-facing surface 432a of the first aperture 430a of the arm 420a engages a proximally-facing ramped surface 534a of the protrusion 530a to urge the protrusion 530a and flexible arm 520a to flex radially inwards. As the flexible arm 520a is flexed radially inwards, the protrusion 530a is disengaged from the first engagement element 540a of the first engagement track 545a.

Disengagement of the protrusion 530a from the first engagement element 540a allows the ratchet collar 510 to move axially with respect to the body 111, for dispensing a first dose of the medicament. Since axial movement of the ratchet collar 510 is no longer limited, the ratchet collar 510 releases the rotary collar 119 for rotation under the bias of the drive member, causing the ratchet collar 510 to move axially in a distal direction due to the interface between the ratchet collar 510 and rotary collar 119. As the ratchet collar 510 moves distally, the protrusion 530a moves distally, passing over the first engagement element 540a of the first engagement track 545a and moving towards the second engagement element 540b of the first engagement track 545a. Rotation of the rotary collar 119 by the drive member simultaneously causes movement of the plunger 121 in the distal direction to dispense the first dose of medicament, due to the interface between the plunger 121 and the rotary collar 119, with the ratchet collar 510 moving towards its position shown in FIG. 5C.

After actuating the actuation member 404 a first time to initiate the medicament delivery, the user may release the actuation member 404 such that it moves proximally from its second axial position back to its first axial position (e.g., under the biasing force of the spring 171).

If the user fails to release the actuation member 404 in sufficient time before the protrusion 530a has moved distally over the first engagement element 540a, the protrusion 530a and flexible arm 520a ay move radially outwards due to the resiliency of the flexible arm 520a, once the protrusion 530a is no longer engaged with the first engagement element 540a. In such circumstances, the protrusion 530a may be received within the first aperture 430a of the arm 430a, with the protrusion 530a moving distally through the first aperture 430a with distal movement of the ratchet collar 510 until the protrusion 530a engages a proximal-facing surface 434a of the first aperture 430a. The proximal-facing surface 434a of the first aperture 430a may be ramped such that protrusion 530a may continue to move distally over the ramped proximal-facing surface 434a of the first aperture 430a. Engagement between the protrusion 530a and the ramped proximal-facing surface 434a causes the protrusion 530a and flexible arm 520a to be moved radially inwards as the ratchet collar 510 continues to move distally. The protrusion 530a will then reach the first guide surface 440a of the arm 420 and continue moving distally across the first guide surface 440a, towards the second engagement element 540b.

Figure 5C:
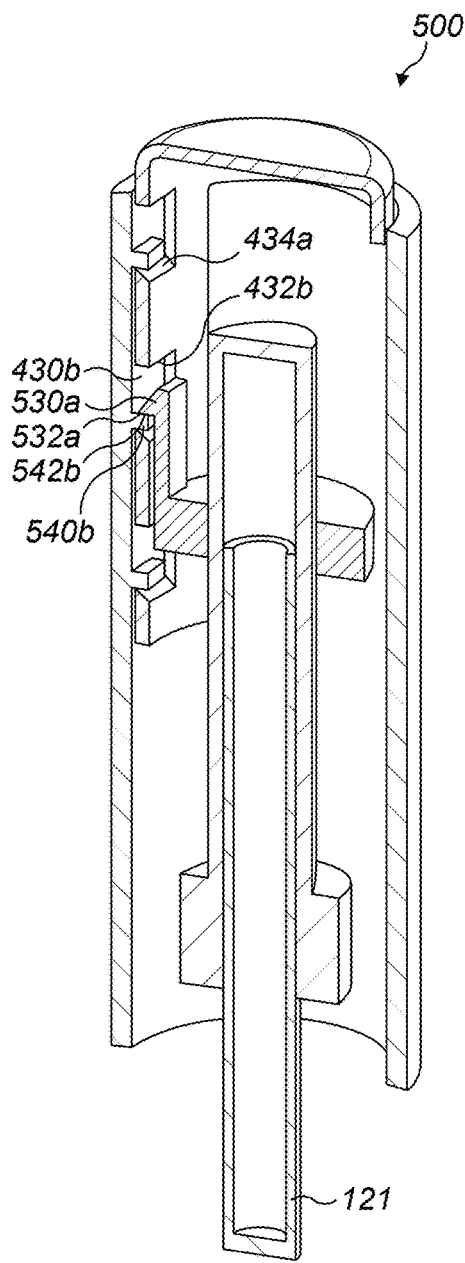
FIG. 5C is a cross-sectional perspective view of a portion of the medicament delivery device of FIG. 5B, after dispensing of the first dose of medicament, and prior to dispensing a second dose of medicament.

If the actuation member 404 is moved from its second axial position back to its first axial position before the protrusion 530a reaches the second engagement element 540b, proximal movement of the actuation member 404 will bring the second aperture 430b of the arm 420a into alignment with the protrusion 530a such that the protrusion 530a is no longer radially supported by the first guide surface 440a. As such, the protrusion 530a moves radially outwards due to the resiliency of the flexible arm 520a, into the second aperture 430b. The protrusion 530a continues moving distally thought the second aperture 430b until it engages the second engagement element 540b of the first engagement track 545a (e.g., the distal-facing engaging surface 532a of the protrusion 530a engages the proximal-facing engaging surface 542b of the second engagement element 540b), at which point further axial movement of the ratchet collar 510 in the distal direction is limited (e.g., prevented) by the engagement between the protrusion 530a and the second engagement element 540b, as shown in FIG. 5C. FIG. 5C shows the ratchet mechanism 505 in its second configuration.

Note that if the actuation member 404 was instead moved from its second position to its first position before the protrusion 530a had moved distally over the entire first engagement element 540a, then the protrusion 530a may avoid being moved radially outwards into the first aperture 430a once it is no longer radially supported by the first engagement element 540a. Instead, the protrusion 530a may move straight onto the first guide surface 440a after it has moved off the first engagement element 540a (or briefly onto the ramped proximal-facing surface 434a before moving onto the first guide surface 440a), before traversing the first guide surface 440a and then second aperture 430b as previously described, until engaging the second engagement element 540b as shown in FIG. 5C.

The axial distance between the first and second engagement elements 540a, 540b, and therefore the distance travelled by the protrusion 530a between the first and second engagement elements 540a, 540b, corresponds to the size (i.e., amount) of the discrete, predetermined first dose of medicament 115 expelled by the medicament delivery mechanism 180. The distance between the first and second engagement elements 540a, 540b may therefore be tailored for different types of medicament 115 and/or different dose regimens etc.

After the first dose of medicament 115 has been dispensed, the user may wish to remove the medicament delivery device 500 from the injection site of the subject. For example, the dose regimen of the medicament 115 may require administration of the medicament 115 to a subject in a plurality of doses, each separated by a sufficient period of time (e.g. three doses to be administered, each dose separated by a week). Additionally or alternatively, the user may wish to use the medicament delivery device 500 to deliver one or more subsequent doses of medicament 115 to a different injection site of the subject (e.g. three doses are to be administered to the subject, each at a different injection sites of the subject). In other examples, the user may wish to use the same medicament delivery device 500 to administer one or more subsequent doses of medicament 115 to a different subject (or subjects) to the subject that received the first dose of medicament 115 (e.g. three doses are to be administered, each dose administered to a different subject, such as a different person). It should be noted that dividing the medicament 115 into three doses for separate administration has been provided merely by way of example, and that in other examples the medicament 115 may be delivered as two doses, or four or more doses. It should also be noted that in some examples, the user may not remove the medicament delivery device 500 from the injection site between the delivery of each dose. Rather, the needle 117 may remain in the injection site after delivery of the first dose and the user may cause a one or more subsequent doses to be delivered to the injection site in succession, for example each dose separated by a dwell time.

Figure 5D:
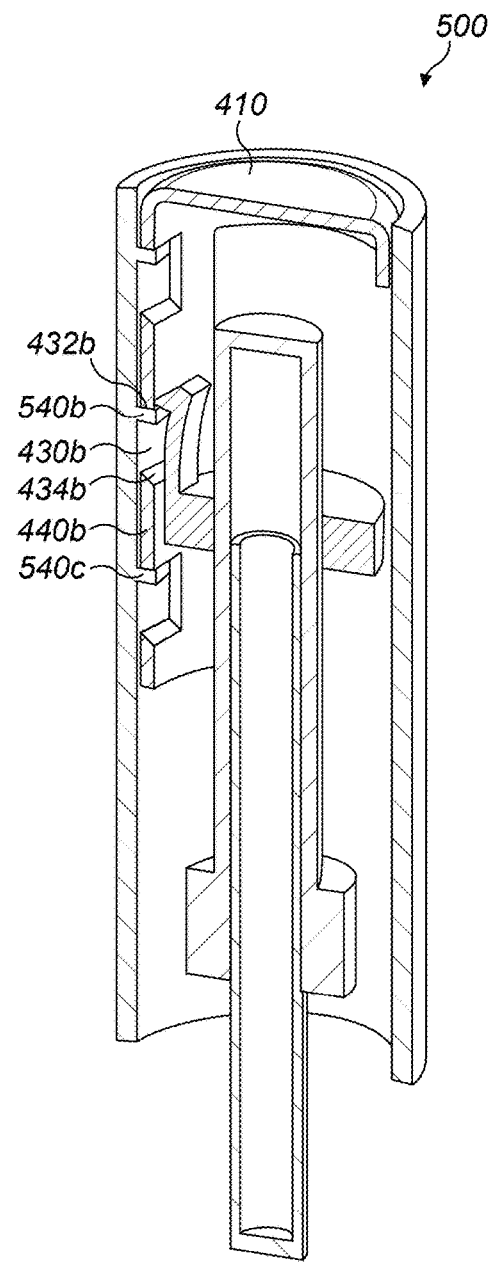
FIG. 5D is a cross-sectional perspective view of a portion of the medicament delivery device of FIG. 5C, during initiation of the dispensing of the second dose of medicament.

To dispense a second dose of medicament 115, the user actuates the actuation member 404 from its first axial position to its second axial position a second time, for example in a similar manner as previously described in relation to FIGS. 5A and 5B. FIG. 5D shows the medicament delivery device 500 of FIG. 5C after the actuation member 404 has been moved from its first axial position to its second axial position with a second actuation action. In a similar manner as previously described in relation to FIG. 5B, the axial movement of the actuation member 404 has disengaged the protrusion 530a, however this time the protrusion 530a is disengaged from a proximally-facing engaging surface 542b of the second engagement element 540b of the first engagement track 545a, rather than from the proximally-facing engaging surface 542a of the first engagement element 540a. Furthermore, the protrusion 530a has been disengaged from the second engagement element 540b by engagement between a distal-facing surface 432b of the second aperture 430b and the proximally-facing ramped surface of the protrusion 530a, rather than engagement between the distal-facing surface 432a of the first aperture 430a and the proximally-facing ramped surface of the protrusion 530a.

Disengagement of the protrusion 530a from the second engagement element 540b causes the ratchet collar 510 and the plunger 121 to move distally relative to the body 111 and rotary collar 119, due to rotation of the rotary collar 119 by the drive member, as described previously.

As the ratchet collar 510 moves distally, the protrusion 530a moves distally, passing over the second engagement element 540b of the first engagement track 545a and moving towards the third engagement element 540c of the first engagement track 545a. Rotation of the rotary collar 119 by the drive member simultaneously causes movement of the plunger 121 in the distal direction to dispense the second dose of medicament, due to the interface between the plunger 121 and the rotary collar 119.

After actuating the actuation member 404 to initiate the delivery of the second dose of medicament 115, the user may release the actuation member 404 such that it moves proximally from its second axial position back to its first axial position (e.g., under the biasing force of the spring 171).

If the user fails to release the actuation member 404 in sufficient time before the protrusion 530a has moved distally over the second engagement element 540b, the protrusion 530a and flexible arm 520a a may move radially outwards due to the resiliency of the flexible arm 520a, once the protrusion 530a is no longer engaged with the second engagement element 540b. In such circumstances, the protrusion 530a may be received within the second aperture 430b of the arm 430a, with the protrusion 530a moving distally through the second aperture 430b with distal movement of the ratchet collar 510 until the protrusion 530a engages a proximal-facing surface 434b of the second aperture 430b. The proximal-facing surface 434b of the second aperture 430b may be ramped such that protrusion 530a may continue to move distally over the ramped proximal-facing surface 434b of the second aperture 430b. Engagement between the protrusion 530a and the ramped proximal-facing surface 434b causes the protrusion 530a and flexible arm 520a to be moved radially inwards as the ratchet collar 510 continues to move distally. The protrusion 530a will then reach the second guide surface 440b of the arm 420a and continue moving distally across the second guide surface 440b, towards the third engagement element 540c.

If the actuation member 404 is moved from its second axial position back to its first axial position before the protrusion 530a reaches the third engagement element 540c, proximal movement of the actuation member 404 will bring the third aperture 430c of the arm 420a into alignment with the protrusion 530a such that the protrusion 530a is no longer radially supported by the second guide surface 440b. As such, the protrusion 530a moves radially outwards due to the resiliency of the flexible arm 520a, into the third aperture 430c. The protrusion 530a continues moving distally thought the third aperture 430c until it engages the third engagement element 540c of the first engagement track 545a (e.g., the distal-facing engaging surface 532a of the protrusion 530a engages the proximal-facing engaging surface 542c of the third engagement element 540c), at which point further axial movement of the ratchet collar 510 in the distal direction is limited (e.g., prevented) by the engagement between the protrusion 530a and the third engagement element 540c, as shown in FIG. 5E. FIG. 5E shows the ratchet mechanism 505 in its third configuration.

Note that if the actuation member 404 was instead moved from its second position to its first position before the protrusion 530a had moved distally over the entire second engagement element 540b, then the protrusion 530a may avoid being moved radially outwards into the second aperture 430b once it is no longer radially supported by the second engagement element 540b. Instead, the protrusion 530a may move straight onto the second guide surface 440b after it has moved off the second engagement element 540b (or briefly onto the ramped proximal-facing surface 434b before moving onto the second guide surface 440b), before traversing the second guide surface 440b and then third aperture 430c as previously described, until the engaging the third engagement element 540c as shown in FIG. 5E.

The axial distance between the second and third engagement elements 540b, 540c, and therefore the distance travelled by the protrusion 530a between the second and third engagement elements 540b, 540c, corresponds to the size (i.e., amount) of the discrete, predetermined second dose of medicament 115 expelled by the medicament delivery mechanism 180. The distance between the second and third engagement elements 540b, 540c may therefore be tailored for different types of medicament 115 and/or different dose regimens etc.

To dispense a third dose of medicament 115, the user once again actuates the actuation member 404 from its first axial position to its second axial position, for example in a similar manner as previously described in relation to FIGS. 5A and 5B. The user may or may not have removed and repositioned the medicament delivery device 500 prior to actuation of the actuation member 404 to dispense the third dose of medicament 115.

FIG. 5F shows the medicament delivery device 500 of FIG. 5E after the actuation member 404 has been moved from its first axial position to its second axial position with a third actuation. In a similar manner as previously described in relation to FIG. 5B, the axial movement of the actuation member 404 has disengaged the protrusion 530a, however this time the protrusion is disengaged from a proximally-facing engaging surface 542c of the third engagement element 540c of the first engagement track 545a, rather than from the proximally-facing engaging surface 542a of the first engagement element 540a. Furthermore, the protrusion 530a has been disengaged from the third engagement element 540c by engagement between a distal-facing surface 432c of the third aperture 430c and the proximally-facing ramped surface of the protrusion 530a, rather than engagement between the distal-facing surface 432a of the first aperture 430a and the proximally-facing ramped surface of the protrusion 530a.

Disengagement of the protrusion 530a from the third engagement element 540c causes the ratchet collar 510 and the plunger 121 to move distally relative to the body and rotary collar 119, due to rotation of the rotary collar 119 by the drive member, as described previously.

As the ratchet collar 510 moves distally, the protrusion 530a moves distally, passing over the third engagement element 540c of the first engagement track 545a. Unlike FIGS. 3A-3K, FIGS. 5A-5G do not show a fourth engagement element 540d of the first engagement track 545a, nevertheless the protrusion 530a would move towards such a fourth engagement element 540d of the first engagement track 545a if present.

Rotation of the rotary collar 119 by the drive member simultaneously causes movement of the plunger 121 in the distal direction to dispense the third dose of medicament, due to the interface between the plunger 121 and the rotary collar 119.

After actuating the actuation member 404 to initiate the delivery of the third dose of medicament 115, the user may release the actuation member 404 such that it moves proximally from its second axial position back to its first axial position (e.g., under the biasing force of the spring 171).

If the user fails to release the actuation member 404 in sufficient time before the protrusion 530a has moved distally over the third engagement element 540c, the protrusion 530a and flexible arm 520a a may move radially outwards due to the resiliency of the flexible arm 520a, once the protrusion 530a is no longer engaged with the third engagement element 540c. In such circumstances, the protrusion 530a may be received within the third aperture 430c of the arm 430a, with the protrusion 530a moving distally through the third aperture 430c with distal movement of the ratchet collar 510 until the protrusion 530a engages a proximal-facing surface 434c of the third aperture 430c. The proximal-facing surface 434c of the third aperture 430c may be ramped such that protrusion 530a may continue to move distally over the ramped proximal-facing surface 434c of the third aperture 430c. Engagement between the protrusion 530a and the ramped proximal-facing surface 434c causes the protrusion 530a and flexible arm 520a to be moved radially inwards as the ratchet collar 510 continues to move distally. The protrusion 530a will then reach the third guide surface 440c of the arm 420a and continue moving distally across the third guide surface 440c, towards, if present, the next engagement element 540 (e.g., towards the fourth engagement element 540d of medicament delivery device 200 of FIGS. 3A-3K).

If the actuation member 404 was instead moved from its second position to its first position before the protrusion 530a had moved distally over the entire third engagement element 540c, then the protrusion 530a may avoid being moved radially outwards into the third aperture 430c once it is no longer radially supported by the third engagement element 540c. Instead, the protrusion 530a may move straight onto the third guide surface 440c after it has moved off the third engagement element 540c (or briefly onto the ramped proximal-facing surface 434c before moving onto the third guide surface 440c), before traversing the third guide surface 440b (and then third aperture 430c, if present, until engaging the fourth engagement element 540d, if present).

Figure 5G:
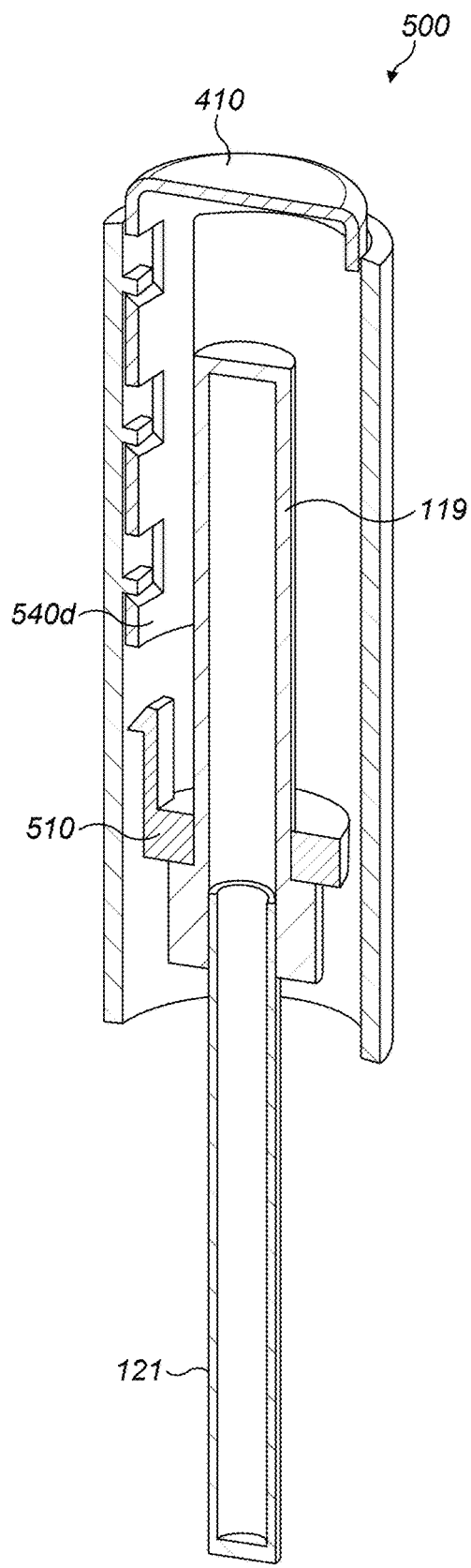
FIG. 5G is a cross-sectional perspective view of a portion of the medicament delivery device of FIG. 5F, after dispensing of the third dose of medicament.

Unlike the medicament delivery device 200 as shown in FIGS. 3A-3K, the medicament delivery device 500 device as shown in FIGS. 5A-5G does not have a fourth aperture 430d of the first arm 420a, nor is a fourth engagement element 540d present in the first engagement track 545a. As such, after the protrusion 530a has moved distally across the third guide surface 440c to the distal end of the third guide surface 440c, the protrusion 530a and flexible arm 520a move radially outwards, towards the inner surface of the body 111, due to the protrusion 530a no longer being radially supported by the third guide surface 440c. The ratchet collar 510 will continue moving distally until it is limited from moving further. For example, FIG. 5G shows a distally-facing surface of the ratchet collar 510 engaging a proximally-facing surface of the rotary collar 119 to limit further distal movement of the ratchet collar 510. In other examples, further distal movement of the ratchet collar 510 may limited by a different mechanism, for example the drive member may no longer provide a biasing force to rotate the rotary collar 119 (e.g., because the spring has depleted its stored elastic energy), or the plunger 121 may engage a stop feature that limits further distal movement of the plunger 121.

It should be noted that in some alternative examples, no guide surface 440 is provided distal to the final engagement element 540. For example, and with reference to FIG. 5G, in some examples the third guide surface 440 is not present (i.e., there is no guide surface 440 distal to the third engagement element 540c). As such, the protrusion 530a may not contact the arm 420a after distally traversing the third engagement element 540c.

FIG. 5G shows the medicament delivery device 500 of FIG. 5F after delivery of the third dose of medicament is complete, with the ratchet mechanism 505 in a fourth configuration.

Returning to FIG. 3A, the actuation member latch 450 is now described.

The actuation member latch 450 is configured to limit distal axial movement of the actuation member 404 from its first axial position to its second axial position. The actuation member latch 450 is movable between a locked configuration, in which distal axial movement of the actuation member 404 from its first axial position to its second axial position is limited (e.g., prevented) by the actuation member latch 450, and an unlocked configuration, in which distal axial movement of the actuation member 404 from its first axial position to its second axial position is allowed (not limited) by the actuation member latch 450. FIG. 3A shows the actuation member latch 450 in the locked configuration, while FIG. 3C shows the actuation member latch 450 in the unlocked configuration.

Figure 4C:
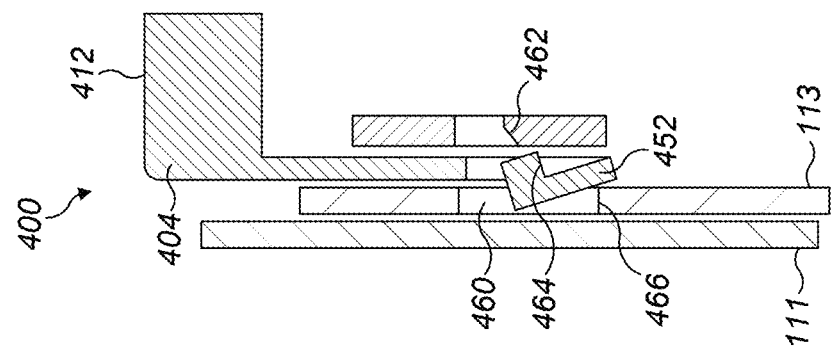
FIG. 4C is a schematic cross-sectional view of a portion of the medicament delivery device of FIG. 4B, showing actuation member latch in the unlocked configuration and the actuation member in a second position.
Figure 4B:
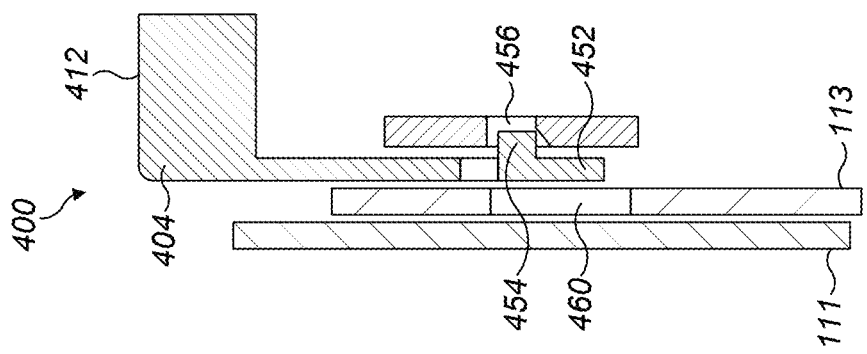
FIG. 4B is a schematic cross-sectional view of a portion of the medicament delivery device of FIG. 4A showing actuation member latch in an unlocked configuration and the actuation member in the first position.
Figure 4A:
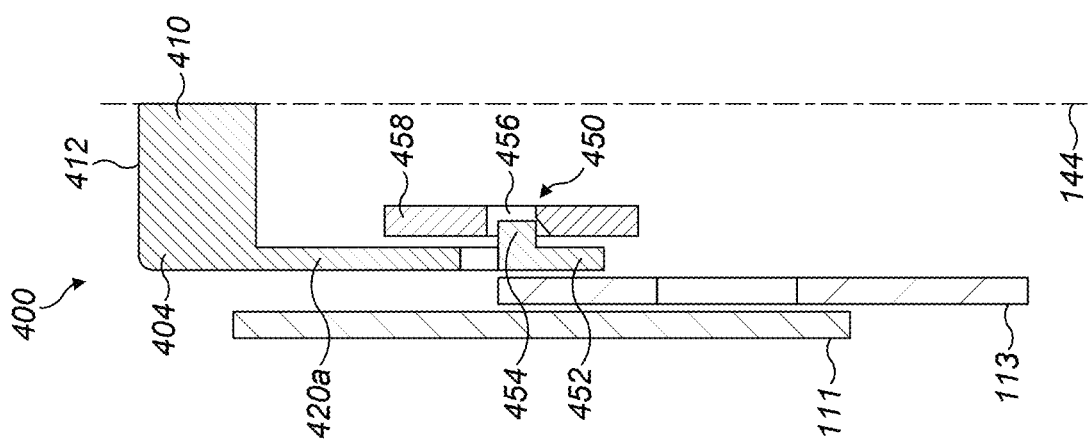
FIG. 4A is a schematic cross-sectional view of a portion of a medicament delivery device in accordance with one or more embodiments, showing an actuation member latch in a locked configuration and an actuation member in a first position.

The actuation member latch 450 is configured to be moved from the locked configuration to the unlocked configuration by the needle cover 113, as described in more detail in relation to FIGS. 4A-4C.

FIGS. 4A-4C show a schematic cross-section of part of a medicament delivery device 400, which may be similar or identical to the medicament delivery device 200, showing various operational states of the actuation member latch 450 in greater detail. FIGS. 4A-4C show only a proximal portion of the medicament delivery device 400, with only the components on one side of the axis 144 shown. Various features of the medicament delivery device 200 that may be present in the medicament delivery device 400 are hidden in FIGS. 4A-4C.

FIG. 4A shows portions of the actuation member 404, actuation member latch 450, needle cover 113 and body 111 of the medicament delivery device 200 when in its first state previously described in relation to FIG. 3A. FIG. 4A shows the actuation member latch 450 in its locked configuration, in which distal axial movement of the actuation member 404 from its first axial position to its second axial position is limited (e.g., prevented) by the actuation member latch 450. The actuation member latch 450 comprises a flexible extension 452 coupled to the arm 420 of the actuation member 404, for example at a distal end of the arm 420. A projection 454 extends from a free end of the flexible extension 452 to engage a recess 456 in a latch element 458. FIG. 4A shows the projection 454 extending radially inwards to engage the recess 456.

FIG. 4A shows the needle cover 113 in its extended position. When in the extended position, the needle cover 113 limits (i.e., prevents) movement of the actuation member latch 450 from its locked configuration to its unlocked configuration. As shown in FIG. 4A, an inner surface of the needle cover 113 is located adjacent the flexible extension 452 such that radial movement of the flexible extension 452 and the projection 454 to disengage the projection 454 from the recess 456 is limited. As such, the needle cover 113 holds the actuation member latch 450 in its locked configuration when the needle cover 113 is in its extended position and, as a consequence, distal movement of the actuation member 404 from its first axial position shown in FIG. 4A to its second axial position shown in FIG. 4C is limited (e.g., prevented).

FIG. 4B shows the portions of the actuation member 404, actuation member latch 450, needle cover 113 and body 111 of the FIG. 4A, once the actuation member latch 450 has been moved from its locked configuration to its unlocked configuration by the needle cover 113.

FIG. 4B shows the needle cover 113 of FIG. 4A after it has been moved proximally with respect to the body 111 from its extended position to its retracted position, for example in response to a user pressing the needle cover 113 against an injection site. As the needle cover 113 has moved proximally, a recess 460 in the needle cover 113 has been brought into radial alignment with the actuation member latch 450 to allow the actuation member latch 450 to be moved from its locked configuration to its unlocked configuration. More specifically, in this example, the recess 460 has been moved into radial alignment with at least a portion of the flexible extension 452 such that the flexible extension 452 is no longer prevented from moving radially outwards by an inner surface of the needle cover 113. Rather, at least a portion of the flexible extension 452 may now be received in the recess 460 of the needle cover 113 when the flexible extension 452 moves radially outwards. The movement of the needle cover 113 has therefore moved actuation member latch 450 from the locked configuration to the unlocked configuration. The recess 460 may be located on the needle cover 113 such that it aligns with the actuation member latch 450 once the needle 117 has reached a desired penetration depth in an injection site.

It can be seen in FIG. 4B that the projection 454 still remains engaged in the recess 456 of the latch element 458. However, distal axial movement of the actuation member 404 from its first axial position to its second axial position is no longer limited (e.g., prevented) by the actuation member latch 450, since distal axial movement of the actuation member 404 from its first axial position (shown in FIG. 4B) to its second axial position (shown in FIG. 4C) will cause the projection 454 to be disengaged from the recess 460, as shown in FIG. 4C. That is, engagement between a distal-facing surface 464 of the projection 454 and a proximal-facing surface 462 of the recess 456 of the latch element 458 during distal movement of the actuation member 404 urges the flexible extension 454 to move radially outwards and into the recess 460 of the needle cover 113, bringing the projection 454 out of engagement with the recess 456 of the latch element 458. In some examples, either or both of the proximal-facing surface 462 and the distal-facing surface 464 may be ramped to assist with urging the projection 454 to disengaged from the recess 456.

As the actuation member 404 moves in a proximal direction relative to the body 111, back from its second axial position shown in FIG. 4C to its first axial position shown in FIG. 4B, the flexible extension 452 moves radially inwards to bring the projection 454 back into engagement with the recess 456 of the latch element 458. This may be due to the flexible extension 452 being resiliently biased to move radially inwards, for example due to at least a portion of the flexible extension being formed from a resilient material.

As the needle cover 113 moves back from its retracted position shown in FIG. 4B to its extended position shown in FIG. 4A, for example due to a user removing the needle cover 113 from an injection site, the needle cover 113 may assist with urging the flexible extension 452 radially inwards to engage the projection 454 with the recess 456, for example due to engagement between a proximal-facing surface 466 of the recess 456 and the flexible extension 452. The actuation member latch 450 is now back in its locked configuration.

Returning to FIG. 3A, the medicament delivery device 200 further has a needle cover guide 143, which may be arranged at least partially within the body 111. The needle cover guide 143 is substantially cylindrical and is rotatable relative to the body 111, for example about the axis 144, but is axially fixed relative to the body 111. FIG. 3A shows the needle cover guide 143 arranged within the distal end 131 of the body 11 of the medicament delivery device 200, however it should be understood that in other examples the needle cover guide 143 may be located at a different location of the medicament delivery device 200, for example proximal to the distal end 131 of the medicament delivery device 200. The needle cover guide 143 comprises a track 128 arranged circumferentially around the needle cover guide 143. In some examples a separate track 128 is provided for each arm 126 (if more than one arm 126a, 126b is present), or a single track 128 may be used for a plurality of arms 126a, 126b.

As shown in FIG. 3A, the needle cover 113 of the medicament delivery device 200 comprises a pair of guide extensions 610a, 610b arranged to engage the track 128. The arm-like guide extensions 610a, 610b extend radially outwards from the remainder of the needle cover 113, such that free ends of the guide extensions 610a, 610b extend within the needle cover guide 143. FIG. 3A shows the guide extensions 610a, 610b extending in a proximal direction from the remainder of the needle cover 113, at a slight acute angle to the axis 144, however it should be understood that the guide extensions 610a, 610b may extend in a different manner to engage the needle cover guide 143. For example, in some examples the guide extensions 610a, 610b may extend substantially radially outwards from the remainder of the needle cover 113, substantially perpendicular to the axis 144.

Each guide extension 610a, 610b has a respective guide protrusion 620a, 620b configured to engage the track 128, such that each guide extension 610a, 610b engages the track 128 via its respective guide protrusion 620a, 620b. FIG. 3A shows the guide protrusions 620a, 620b at the free (e.g., proximal) end of each guide extension 610a, 610b, although in other embodiments the guide protrusions 620a, 620b may be located distally from the free end of the guide extensions 610a, 610b. The guide extensions 610a, 610b and/or guide protrusions 620a, 620b may be flexible, as discussed later.

The track 128 is configured to be engaged by the one or more guide protrusions 620a, 620b of the needle cover 113 such that an axial movement of the needle cover 113 from the extended position to the retracted position causes a rotation of the needle cover guide 143 relative to the needle cover 113.

FIGS. 6A-6F show the various operations of the needle cover guide 143 and the needle cover 113 of the medicament delivery device 200 in more detail.

FIG. 6A shows a perspective view of the needle cover guide 143 and the needle cover 113 of the medicament delivery device 200 when in its first state shown in FIG. 3A. Only a distal portion of the needle cover 113 including the guide extensions 610 and respective guide protrusions 620 is shown. Various other features of the medicament delivery device 200 may be hidden for clarity.

FIG. 6A shows the needle cover guide 143 comprising a tool engagement feature 670 arranged at a distal end of the needle cover guide 143, the purpose of which shall be explained later.

The track 128 is configured to limit a proximal movement of the needle cover 113 relative to the body 111, after the needle cover 113 has moved from the retracted position back to the extended position. That is, the or each guide extension 610 is configured to engage the track 128 via its respective guide protrusion 620 such that a proximal movement of the needle cover 113 is limited after the needle cover 113 has moved from the retracted position to the extended position.

FIG. 6A shows the track 128 comprising a plurality of track portions 630a-630f arranged circumferentially around the needle cover guide 143. FIG. 6A shows the track 128 comprising six track portions 630a-630f, however it should be understood that this is not meant to be limiting and that in other examples fewer than six (i.e., from one to five) or greater than six track portions 630a-630f may be present.

Each track portion 630a-630f generally comprises a respective first region 641, second region 642 and third region 643. However, in some examples the first track portion 630a does not comprise a third region 641. Additionally or alternatively, in some examples, at least one of the track portions 630b-630f does not comprise a first region 641 and/or second region 642.

FIG. 6A shows each first region 641, second region 642 and third region 643 of the track portions 630a-630f formed as apertures/cut-outs in the needle cover guide 143. However, it should be understood that this is not meant to be limiting and that in other examples, one or more (e.g., all) of the first region 641, second region 642 and third region 643 of the track portions 630a-630f may be in the form of grooves in the internal surface of the needle cover guide 143 (or external surface of the needle cover guide 143, if the guide extensions 610 are extend radially outside of the needle cover guide 143).

FIG. 6A shows each guide extension 610a, 610b extending in a substantially proximal direction, within the needle cover guide 143. The guide protrusions 620a, 620b extend radially outwards from their respective guide extension 610a, 610b such that they are each retained within a respective track portions 630a-630f of the track 128. In this example, one guide protrusion 620a engages a first of the track portions 630a while the other guide protrusion 620b engages a fourth of the track portions 630d. Each guide protrusion 620a, 620b is currently at a respective first position 651 within the first region 641 of its respective track portion 630a, 630d.

Returning to FIG. 3A, an example operation of the medicament delivery 200 to dispense a plurality of discrete doses of medicament shall now be described.

In the first state of the medicament delivery device 200 shown in FIG. 3A, movement of the actuation member 404 from its first axial position to its second axial position is initially limited (e.g., prevented) due to the actuation member latch 450 being in its locked configuration, (e.g., as previously described in relation to FIG. 4A).

A user may begin a medicament delivery process to dispense a first dose of the medicament 115 by placing a distal end 120 of the needle cover 113 against an injection site of a subject. The subject may be a human or an animal. In some examples the user is also the subject (i.e., in the case of self-injection), however in other examples the user and subject are different people (e.g., the user is a healthcare professional and the subject is a patient).

After placing the distal end 120 of the needle cover 113 against the injection site, the body 111 is moved towards the injection site, causing relative movement between the needle cover 113 and the body 111 as the needle cover 113 translates in the proximal direction from its extended position to its retracted position. As the needle cover 113 is moved distally, the needle cover 113 moves the actuation member latch 450 from its locked configuration to its unlocked configuration (e.g., as previously described in relation to FIGS. 4A and 4B), unlocking the actuation member 404 such that it may now be actuated.

FIG. 3B shows the medicament delivery device 200 of FIG. 3A in a second state, wherein the needle cover 113 has been moved to its retracted position against the biasing force of the needle cover biasing member 118 and the actuation member latch 450 has been moved to its unlocked configuration (e.g., e.g., as previously described in relation to FIGS. 4A and 4B). As the needle cover 113 has moved proximally, the distal end 140 of the needle 117 has become progressively uncovered, allowing it to penetrate the injection site. Medicament delivery has not yet been initiated, due to the ratchet mechanism 505 still limiting movement of the medicament delivery mechanism 180 (e.g., as previously described in relation to FIG. 5A).

Proximal movement of the needle cover 113 has caused rotation of the needle cover guide 143 due to interaction between the guide arms 610 and the track 128, as now explained in relation to FIG. 6B.

FIG. 6B shows the configuration of the needle cover guide 143 and needle cover 113 once the medicament delivery device 200 has moved from its first state shown in FIG. 3A to its second state shown in FIG. 3B.

Proximal movement of the needle cover 113 relative to the body 111 and needle cover guide 143 (as indicated by arrow 682) has rotated the needle cover guide 143 (as indicated by arrow 684) due to engagement between the guide protrusions 620 and their respective track portions 630a, 630d. Proximal movement of the needle cover 113 relative to the body 111 has moved the guide protrusions 620a, 620b proximally relative to the needle cover guide 143 such that the guide protrusions 620a, 620b traverse the first region 641 of their respective track portions 630a, 630d, from their respective first positions 651 in the respective first regions 641 to respective second positions 652 in their respective second regions 642.

The first regions 641 each extend circumferentially and axially around the needle cover guide 143 (e.g., helically), with each first region 641 extending at an angle to the axis 144. The second positions 652 are each located proximal to the first positions 651, and spaced circumferentially from the first positions 651 around the needle cover guide 143. The first regions 641 are shaped such that engagement between the guide protrusions 620a, 620b and the respective first regions 641 as the guide protrusions 620a, 620b traverse the respective first regions 641 converts proximal axial movement of the needle cover 113 into rotation of the needle cover guide 143 (e.g. by engagement between each guide protrusion 620a, 620b and a respective angled proximal wall 680 of the respective first region 541). Proximal movement of guide protrusions 620a, 620b beyond the second positions 652 may be limited by engagement between the guide protrusions 620a, 620b and respective distal-facing surfaces 660 of the second regions 642.

Returning to FIG. 3B, the user may now initiate delivery of the first dose of medicament 115 by actuating the actuation member 404, for example as previously described in relation to FIG. 5B. The user may actuate the actuation member 404 by pushing the proximal actuation surface 412 of the button 410 in the distal direction, causing the actuation member 404 to move distally from its first axial position (shown in FIG. 3B) to its second axial positions (shown in FIG. 3C), against the biasing force provided by the spring 171.

FIG. 3C shows the medicament delivery device 200 of FIG. 3B in a third state, in which medicament delivery has been initiated to dispense a first dose of medicament, for example as previously described in relation to FIG. 5B. Movement of the actuation member 404 from its first axial position to its second axial position has caused the projection 454 of the actuation member latch 450 to disengage the recess 456 of the latch element 458 (e.g., as previously described in relation to FIG. 4C).

Figure 3D:
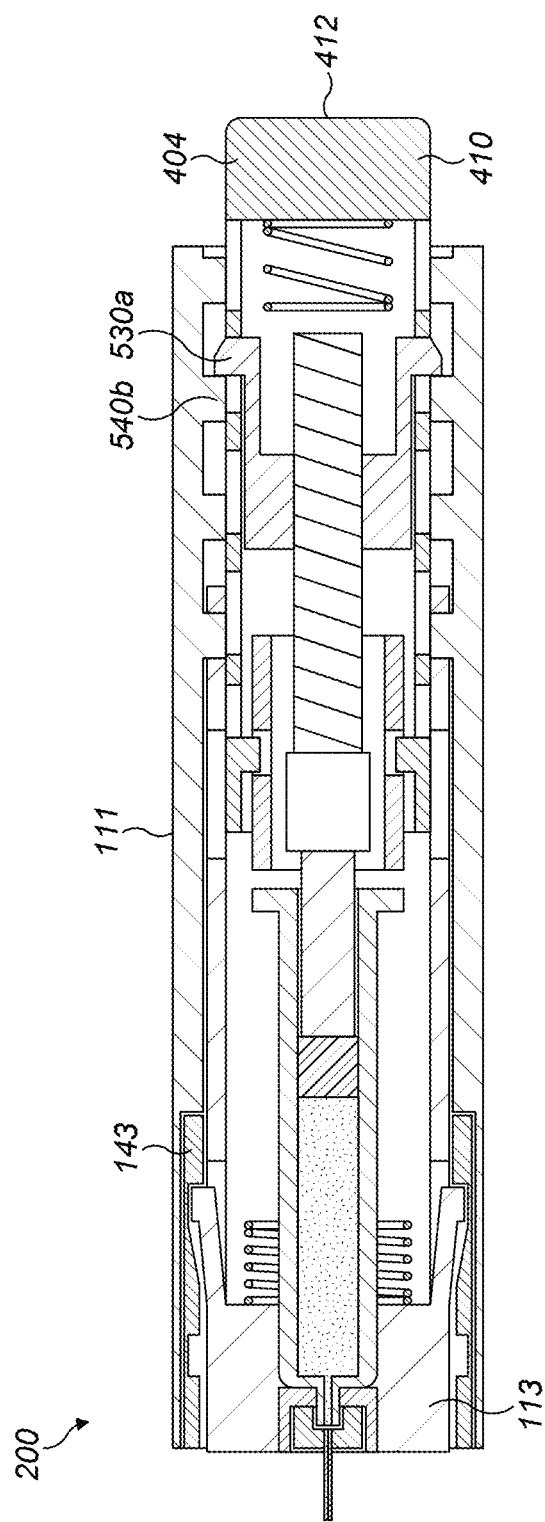
FIG. 3D is a schematic cross-sectional view of the medicament delivery device of FIG. 3C, in a fourth state.

FIG. 3D shows the medicament delivery device 200 of FIG. 3C in a fourth state, after the user has released the actuation member 404, allowing the actuation member 404 to move from its second axial position back to its first axial position due to the biasing force exerted by the spring 171. A first dose of the medicament 115 has been dispensed by the medicament delivery mechanism 180, via distal movement of the plunger 121 and piston 123 (e.g., as previously described in relation to FIGS. 5B and 5C). The ratchet mechanism 505 is in its second configuration.

The actuation member latch 450 remains in its unlocked state while the needle cover 113 remains in its retracted state. Nevertheless, the projection 454 of the actuation member latch 450 may have re-engaged the recess 456 of the latch element 458 during the movement of the actuation member 404 (e.g., as previously described in relation to FIGS. 4B and 4C).

Figure 3E:
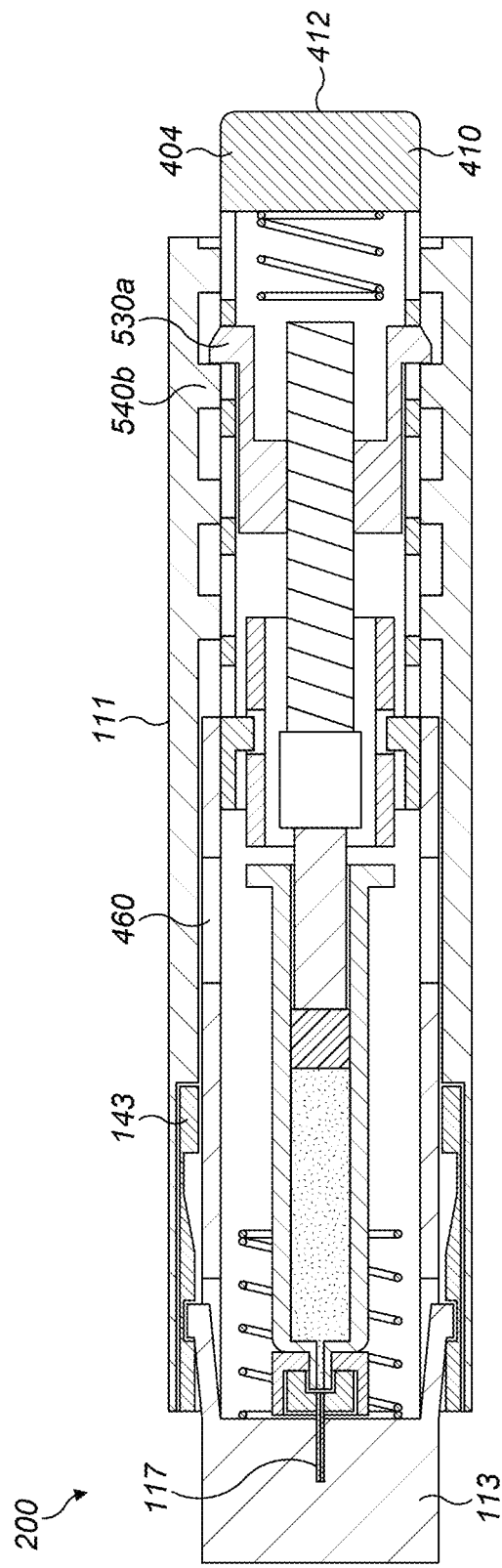
FIG. 3E is a schematic cross-sectional view of the medicament delivery device of FIG. 3D, in a fifth state.

FIG. 3E shows the medicament delivery device 200 of FIG. 3D in a fifth state, after the user has removed the medicament delivery device 200 from the injection site. As the body 111 of the medicament delivery device 200 has been moved away from the injection site, the needle cover 113 has moved distally from its retracted position shown in FIG. 3D to its extended position shown in FIG. 3E under the biasing force of the needle cover biasing member 118, and in doing so has covered the needle 117 to protect the user and/or subject from an accidental needle-stick event.

As the needle cover 113 has moved back to its extended position, the recess 460 of the needle cover 113 has moved out of radial alignment with the actuation member latch 450 such that the actuation member latch 450 has been moved from its unlocked position to its locked position (e.g., as previously described in relation to FIGS. 4A-4C), limiting actuation of the actuation member 404.

Figure 6D:
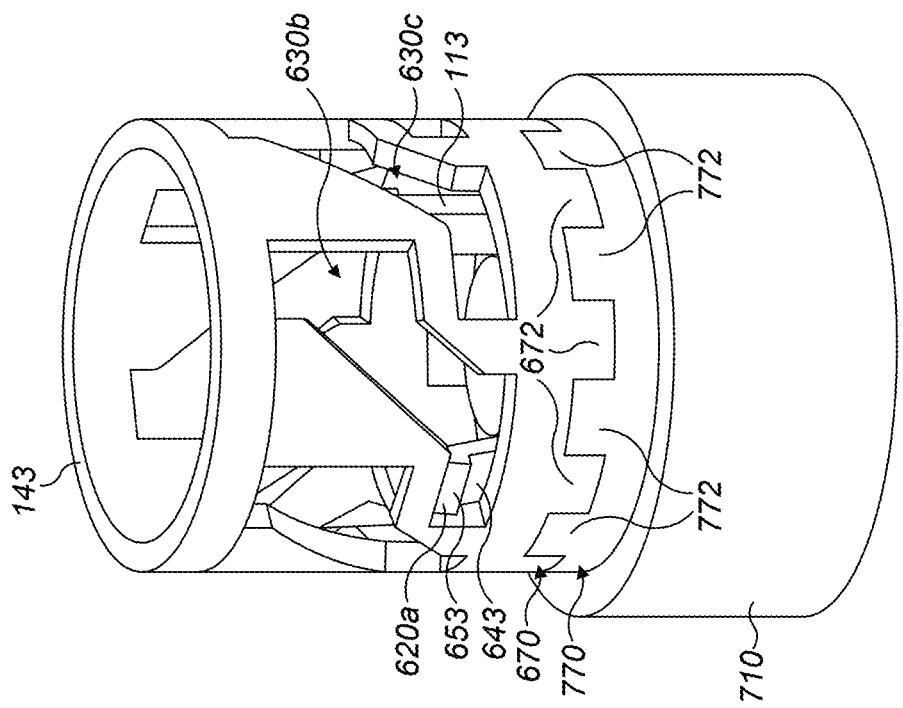
FIG. 6D is a perspective view of a needle cover guide and portion of a needle cover of the medicament delivery device of FIG. 3F, after coupling of a needle unit tool.
Figure 6C:
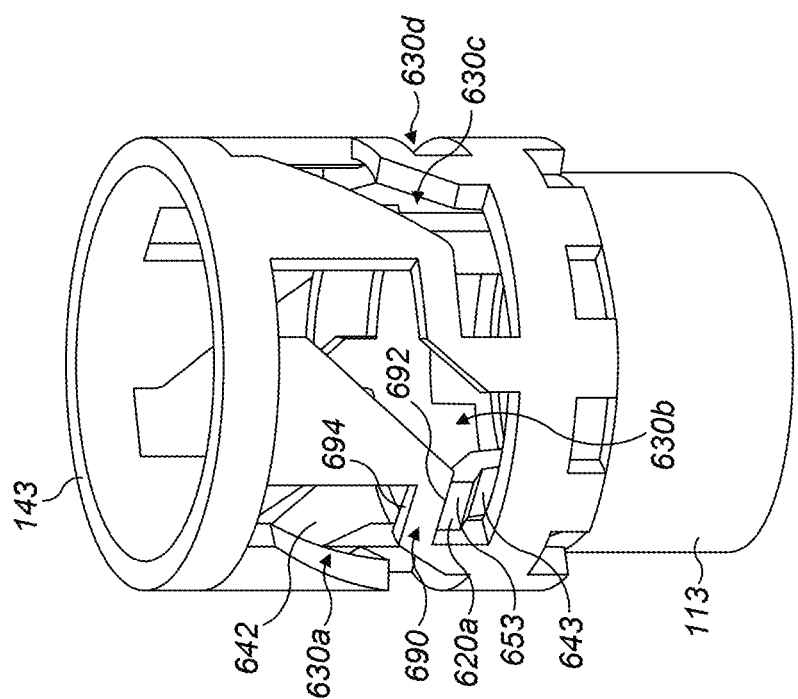
FIG. 6C is a perspective view of a needle cover guide and portion of a needle cover of the medicament delivery device of FIG. 3E.

As the needle cover 113 moves back from its retracted position shown in FIG. 3D to its extended position shown in FIG. 3E, the needle cover 113 is locked by the needle cover guide 143 to limit subsequent proximal movement of the needle cover 113 from the extended position to the retracted position, as now described in relation to FIG. 6C.

As shown in FIG. 6C, each second region 642 of each track portion 630 extends axially across the needle cover guide 143, to allow the guide protrusion 620 to move distally from the second position 652 as the needle cover 113 moves from its retracted position to its extended position.

For each track portion 630 arranged around the needle cover guide 143, the third region 643 of that adjacent track portion 630 may be located distal to the second region 642 of the previous track portion 630 (i.e., the previous, adjacent track portion 630 arranged around the circumference of the needle cover guide 143). For example, FIG. 6C shows the third region 643 of the second track portion 630b located distal to the second region 642 of the first track portion 630a.

The arrangement of the track portions 630 is such that distal movement of the needle cover 113 from its retracted position to its extended position causes the guide protrusions 620 to travel distally through a respective second region 642 of a respective track portion 630 into a respective third region 643 of the next track portion 630, from their respective second position 652 in their respective second region 642 to a respective third position 653 in their respective third region 643, wherein the third positions 653 are each distal to the second positions 652, but axially aligned.

For example, and as shown in FIG. 6C, distal movement of the needle cover 113 from its retracted position shown in FIG. 6B to its extended position shown in FIG. 6C causes the guide protrusion 620a in the first track portion 630a to travel distally through a the second region 642 of the first track portion 630a into a third region 643 of the second track portion 630b, from its second position 652 in the second region 642 of the first track portion 630a to a third position 653 in the third region 643 of the second track portion 630b.

The second regions 642 and third regions 643 are arranged such that the needle cover guide 143 is not substantially rotated relative to the needle cover 113 by the distal movement of the needle cover 113 relative to the needle cover guide 143, as shown in FIG. 6C.

FIG. 6C shows a locking element 690 arranged between the first track portion 630*a* and the second track portion 630*b*, between the second region 642 of the first track portion 630*a* and the third region 643 of the second track portion 630*b*.

The locking element 690 is arranged to lock the needle cover 113 in its extended position after the needle cover 113 has moved from its retracted position to its extended position. That is, the locking element 690 is arranged such that an axial movement of the needle cover 113 from the retracted position to the extended position (subsequent to the rotation of the needle cover guide 143 previously described in relation to FIG. 6B) engages the guide protrusion 620 with the locking element 690, to limit (e.g., prevent) a further axial movement of the needle cover 113 from the extended position to the retracted position. The guide protrusion 620*a* moves over the locking element 690 as the guide protrusion 620*a* travels from the second region 642 of the first track portion 630*a* to the third region 643 of the second track portion 630*b*. Once the guide protrusion 620*a* reaches its third position 653 in the third region 643 of the second track portion 630*b*, the guide protrusion 620*a* becomes engaged with the locking element 690 to limit proximal movement of the needle cover 113 relative to the needle cover guide 143.

For example, the locking element 690 may comprise a proximally-facing ramped surface 692 and a distally-facing locking surface 694, the distally-facing locking surface 694 located distal to the ramped surface 692. As the guide protrusion 620*a* moves distally from the second region 642 of the first track portion 630*a* to the third region 643 of the second track portion 630*b*, it engages and traverses the proximally-facing ramped surface 692, which causes the respective guide extension 610*a* (on which the guide protrusion 620*a* is located) to flex radially inwards, moving the guide protrusion 620*a* radially inwards. As the guide protrusion 620*a* continues to move distally and passes the distal end of the ramped surface 692, the guide protrusion 620*a* is no longer radially supported by the ramped surface 692 and so is moved radially outwards as the guide extension 610*a* flexes radially outwards (e.g., due to the resilient nature of the guide extension 610*a*), passing over the locking surface 694 of the locking element 690. The guide protrusion 620*a* is now located distal to the locking surface 694, with the locking surface 694 limiting proximal movement of the needle cover 113 relative to the needle cover guide 143 due to engagement between the guide protrusion 620*a* (of a different portion of the guide extension 610*a*) and the locking surface 694.

It should be noted that in some examples, a respective locking element 690 may be located between each second region 642 and adjacent third region 643. In other examples, a respective locking element 690 may be located between less than all second regions 642 and adjacent third regions 643.

Returning to FIG. 3E, since the needle cover 113 is now limited from moving proximally from its extended position to its retracted position due to engagement with the locking element 690 of the needle cover guide 143, the needle cover 113 cannot presently move to its retracted position to unlock the actuation member latch 450, which in turn means that the actuation member 404 cannot presently be actuated to initiate delivery of the second dose of medicament 115.

To unlock the needle cover 113 from the locking element 690 such that it can be retracted again, the user can rotate the needle cover guide 143 relative to the needle cover 113 and body 111, to disengage the guide protrusion(s) 620*a*, 620*b* from the respective locking element(s) 690. This rotation may be achieved using a needle unit tool 710, such as the needle unit tool 710 shown in FIG. 3F.

The needle unit tool 710 is a device that is releasably couplable to the needle cover guide 143. The needle unit tool 710 comprises a tool engagement feature 770 configured to engage a corresponding tool engagement feature 670 of the needle cover guide 143 for rotating the needle cover guide 143 about the axis 144, relative to the needle cover 113.

In some examples, the needle unit tool 710 may also be configured for performing an operation to replace the needle unit 116 coupled to the syringe 150. For example, the needle unit tool 710 may be configured for removing (i.e., uncoupling) the needle unit 116 from the syringe 150 and/or for coupling a new needle unit 116 to the syringe 150.

Configuring the needle cover guide 143 such that it can be rotated by a needle unit tool 710 as the needle unit tool 710 performs a needle unit 116 replacement operation e.g., uncoupling and/or coupling a needle unit 116) may be beneficial, since linking the unlocking of the needle cover 113 with the replacement of a needle unit 116 may remind/ and or force the user to replace the needle unit 116 after each dose of medicament 115 has been dispensed. That is, the user will be required to replace the needle unit 116 using the needle unit tool 710 before the medicament delivery device 200 will allow a subsequent dose of medicament 115 to be dispensed. Guiding the user to replace the needle unit 116 after each dose is delivered may improve the safety of the medicament delivery device 200, since it may reduce the likelihood of contamination and/or discomfort associated with the reuse of a needle 117.

In some examples, the same needle unit tool 710 may be used to couple and uncouple a needle unit 116 from the medicament delivery device 200. In such examples, the needle unit tool 710 may be configured to rotate the needle cover guide 143 during only one of coupling and uncoupling of a needle unit 116 (e.g., the needle unit tool 710 may be configured to rotate the needle cover guide 143 during uncoupling of a needle unit 116 but not coupling of a needle unit 116, or the needle unit tool 710 may be configured to rotate the needle cover guide 143 during coupling of a needle unit 116 but not uncoupling of a needle unit 116. For example, if the needle unit 116 is configured to be both coupled and uncoupled to the medicament delivery device 200 using a screw connection, a needle unit tool 700 such as the needle unit tool 700' later described in relation to FIG. 7 may be used. In other examples, if the needle unit 116 is configured to be one of coupled and uncoupled to the medicament delivery device 200 using a rotational (e.g., screw) connection and the other of coupled and uncoupled to the medicament delivery device 200 using a connection that requires axial but not rotational relative rotation (e.g., a snap fit connection), the same needle unit tool 710 may be used for both coupling and uncoupling the needle unit 116 (e.g., by performing axial but not rotational movement of the needle unit tool 710 relative to the medicament delivery device 200 to uncouple a used needle unit 116, followed by rotational movement of the needle unit tool 710 relative to the medicament delivery device 200 to couple a new needle unit 116 to the medicament delivery device 200, or vice versa).

In other examples, one needle unit tool 710 may be used to perform uncoupling of a needle unit 116 from the medicament delivery device 200, while a different needle unit tool 710 may be used to perform coupling of a needle unit 116 to the medicament delivery device 200, where only one of the needle unit tools 710 may be configured to engage the needle cover guide 143 for rotation as it couples/uncouples the needle unit 116.

Figure 3F:
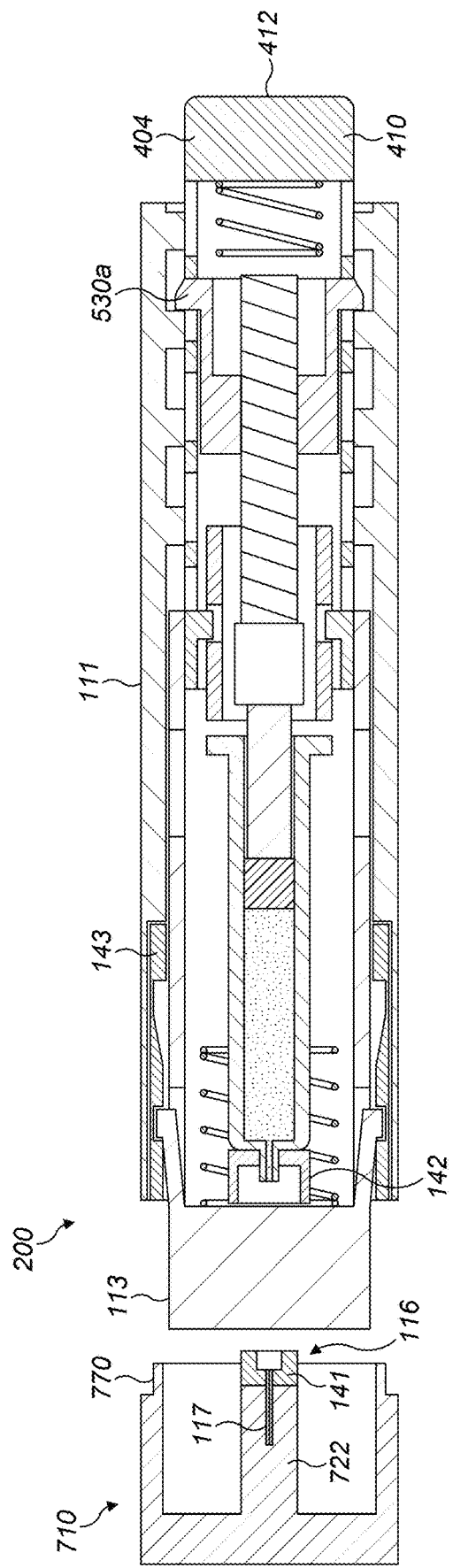
FIG. 3F is a schematic cross-sectional view of the medicament delivery device of FIG. 3E, in a sixth state.

FIG. 3F shows the medicament delivery device 200 of FIG. 3E in a sixth state, after the user has removed the needle unit 116 from the medicament delivery device 200, and an example of a needle unit tool 710.

The needle unit tool 710 may have a substantially cylindrical form, and comprises a needle unit holder 722 configured to be releasably coupled to a needle unit 116 during coupling and/or uncoupling of the needle unit 116 to the medicament delivery device 200. The needle unit holder 722 may be configured to be releasably coupled to the needle unit 116 using any suitable means, for example by a friction fit, screw connection, adhesive (e.g., glue) connection, snap fit, magnetic connection etc.

The user may have uncoupled the used needle unit 116 from the medicament delivery device 200 using the needle unit tool 710 having the tool engagement feature 770, or by a needle unit tool 710 (or other means) without the tool engagement feature 770. For example, the user may have first coupled the needle unit holder 722 of the needle unit tool 710 to the needle unit 116 by moving the needle unit tool 710 in a proximal direction relative to the needle unit 116 until the needle unit holder 722 engages and couples to the needle unit 116. The needle unit holder 122 may have been inserted through a distal opening in the needle cover 113 to engage the needle unit 116.

The user may then uncoupled the needle unit 116 from the medicament delivery device 200 by moving the needle unit tool 710 relative to the medicament delivery device 200. For example, where the needle unit 116 is coupled to the medicament delivery device 200 by a screw connection (e.g., Luer lock connection) between the connection interface 141 of the needle unit 116 and the connection interface 142 of the syringe 150, the needle unit tool 710 may be rotated relative to the medicament delivery device 200 about the axis 144 and moved distally relative the medicament delivery device 200 to unscrew the needle unit 116 from the medicament delivery device 200. In other examples, where the needle unit 116 is coupled to the medicament delivery device 200 by a snap fit connection between the connection interface 141 of the needle unit 116 and the connection interface 142 of the syringe 150, the needle unit tool 710 may be moved distally relative to the medicament delivery device 200 (in some examples without relative rotation) such that the connection interface 141 of the needle unit uncouples from the connection interface 142 of the syringe 150.

Additional/alternative mechanisms and/or movements to those disclosed herein for using the needle unit tool 710 (or another means) to uncouple the needle unit 116 from the medicament delivery device 200 may be used, the selection of which may depend on the type of connection between the needle unit 116 and the medicament delivery device 200.

In this example, it shall be assumed that the user has removed the used needle unit 710 from the medicament delivery device 200 using a needle unit removal tool 710 that has not rotated the needle cover guide 143 during uncoupling of the needle unit 710 from the medicament delivery device 200. FIG. 3F shows that removal of the needle unit 116 has not rotated the needle cover guide 143. As such, the needle cover 113 remains inhibited from moving from its extended position to its retracted position due to engagement with the locking element 690.

Figure 3G:
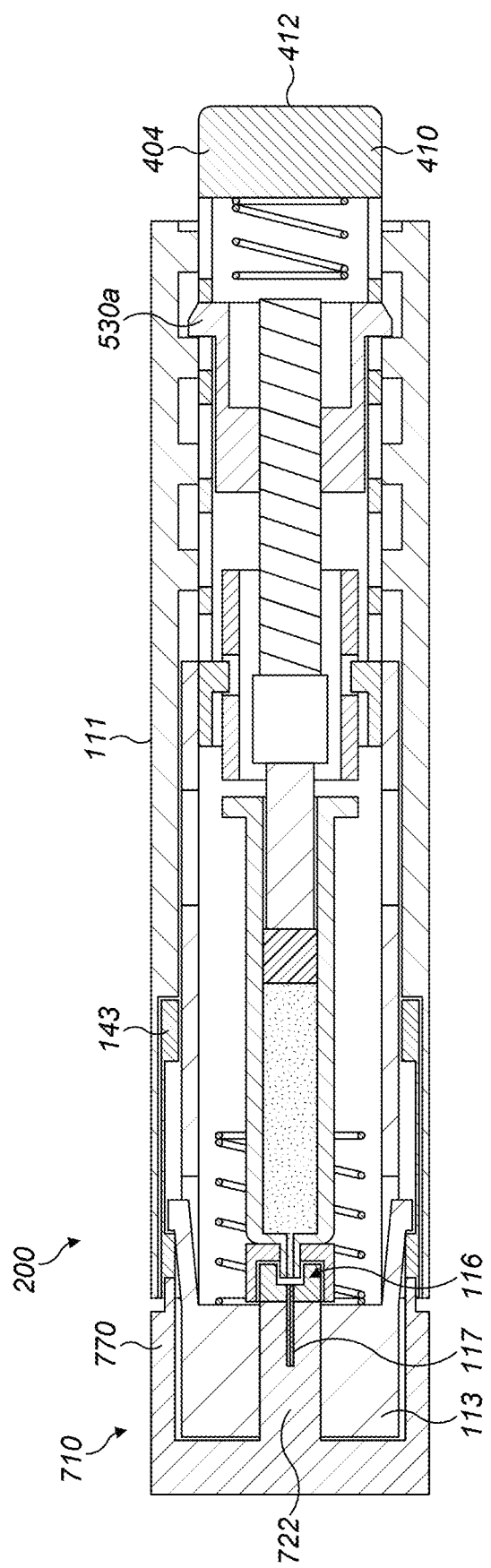
FIG. 3G is a schematic cross-sectional view of the medicament delivery device of FIG. 3F, in a seventh state.

FIG. 3G shows the medicament delivery device 200 of FIG. 3F in a seventh state, after the user has coupled a new needle unit 116 to the syringe 150 using a needle unit tool 710.

In some examples, the needle unit tool 710 may be provided to the user with a new needle unit 116 already coupled to the needle unit holder 772, ready for attachment to the syringe 150. In other examples, the user may couple the new needle unit 116 to the needle unit holder 772 prior to using the needle unit tool 710 to couple the new needle unit 116 to the syringe 150. If the same needle unit tool 710 is being used to uncouple the used needle unit 116 and couple the new needle unit116, the user may remove the used needle unit 116 from the needle unit tool 710 prior to coupling a new needle unit 116 to the needle unit tool 710 (e.g., using the needle unit holder 722).

As shown in FIG. 3G, the needle unit tool 710 has been brought into engagement with the distal end of the medicament delivery device 200 by moving the needle unit tool 710 proximally towards the distal end of the medicament delivery device 200, such that the new needle unit 116 has passed through the opening at the distal end 120 of the needle cover 113. The connection interface 141 of the new needle unit 116 engages the connection interface 142 of the syringe 150 (e.g., by any suitable motion disclosed herein). The tool engagement feature 770 of the needle unit tool 710 has also been brought into engagement with the tool engagement feature 670 of the needle cover guide 143.

In this example, the connection interface 141 of the new needle unit 116 is to be coupled to the connection interface 142 of the syringe 150 at least by a rotation of the needle unit tool 710 and new needle unit 116 relative to the syringe 150, about the axis 144. This rotation also causes the needle cover guide 143 to be rotated due to engagement between the tool engagement feature 770 of the needle unit tool 710 and the tool engagement feature 670 of the needle cover guide 143. FIG. 3G shows the needle cover guide 143 after it has been rotated during attachment of the new needle unit 116.

FIG. 6D shows the configuration of the needle cover guide 143 and needle cover 113 of the medicament delivery device 200 when in its sixth state shown in FIG. 3F, prior to rotation of the needle cover guide 143 by the needle unit tool 710. It can be seen that the guide protrusions 620a, 620b remain in their respective third positions 653 in the respective third regions 643.

FIG. 6D also shows the needle unit tool 710 when coupled to the needle cover guide 143. The needle unit holder 722 and the new needle unit 116 have been hidden for clarity. The distal end of the needle cover 113 is received within the needle cover tool 710 (e.g., in a annular groove).

The tool engagement feature 770 of the needle unit tool 710 has been brought into engagement with the tool engagement feature 670 of the needle cover guide 143. In this example, the tool engagement feature 770 of the needle unit tool 710 comprises a plurality of teeth 772 arranged to engage a plurality of teeth 672 that form the tool engagement feature 670 of the needle cover guide 143. FIG. 6D shows the teeth 672 arranged in a circular pattern to extend distally from the distal circumferential end surface of the needle cover guide 143. The teeth 772 are also arranged in a circular pattern, and extend proximally from a proximal-facing surface of the needle unit tool 710 (when the needle unit tool 710 is coupled to the needle cover guide 143). The tool engagement feature 770 of the needle unit tool 710 engages the tool engagement feature 670 of the needle cover guide 143 such that a rotation of the needle unit tool 710 about the axis 144 will cause a corresponding rotation of the needle cover guide 143.

Figure 6F:
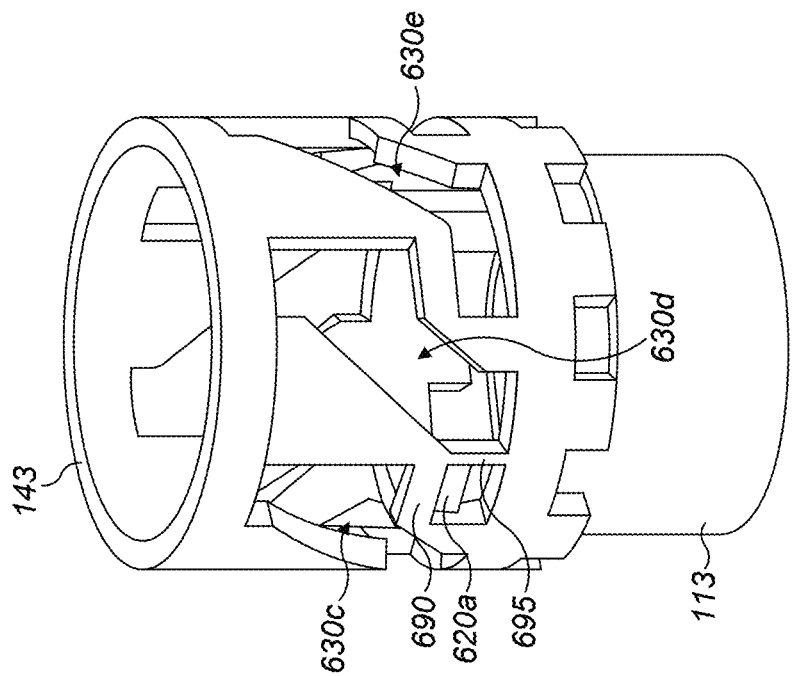
FIG. 6F is a perspective view of a needle cover guide and portion of a needle cover of the medicament delivery device of FIG. 3K.
Figure 6E:
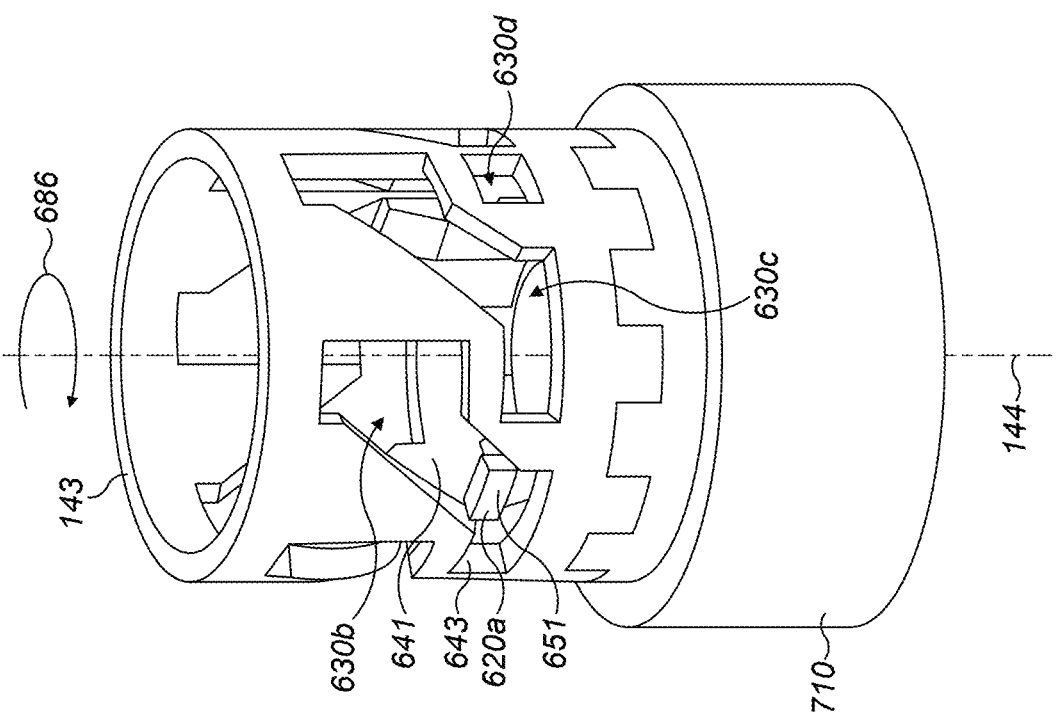
FIG. 6E is a perspective view of a needle cover guide and portion of a needle cover of the medicament delivery device of FIG. 3G.

FIG. 6E shows the configuration of the needle cover guide 143 and needle cover 113 of the medicament delivery device 200 when in its seventh state shown in FIG. 3G, after rotation of the needle cover guide 143 by the needle unit tool 710. As the needle cover tool 710 has been rotated about the axis 144 as indicated by the arrow 686, the needle cover guide 143 has rotated in concert with the needle unit tool 710, from its rotational position shown in FIG. 6D to its rotational position shown in FIG. 6E. It can be seen that the guide protrusions 620 have moved circumferentially around the track 128 from their respective third positions 653 in the third regions 643 of their respective track portions 630b, 630e to first positions 651 in the first regions 641 of their respective track portions 630b, 630e. The guide protrusions 620 are therefore in similar positions in FIG. 6E as they were in FIG. 6A.

As shown in FIG. 6E, the rotation of the needle cover guide 143 relative to the needle cover 113 has moved the guide protrusions 620a, 620b out of engagement with their respective locking element(s) 690, to allow the further axial movement of the needle cover 113 from the extended position to the retracted position.

Returning to FIG. 3G, the user may remove the needle unit tool 710 from the medicament delivery device 200 once the new needle unit 116 has been coupled and the needle cover guide 143 rotated, in preparation for administering a second dose of the medicament 115.

Figure 3H:
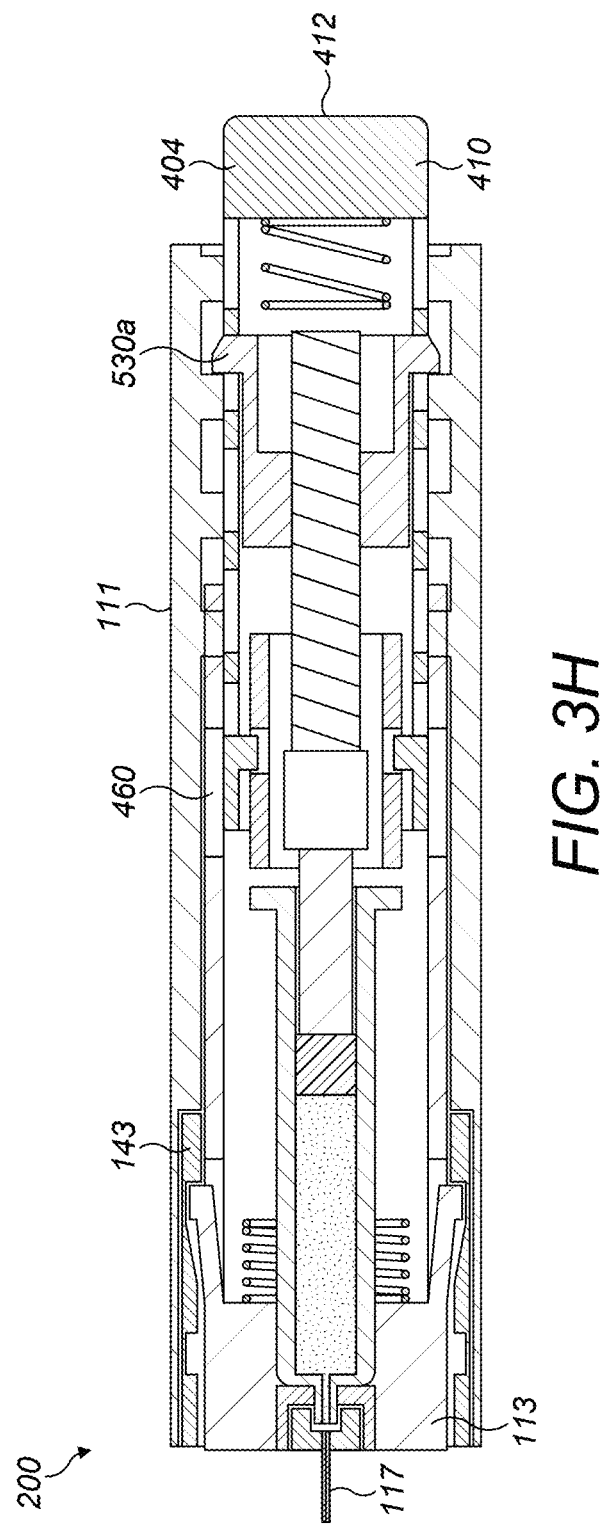
FIG. 3H is a schematic cross-sectional view of the medicament delivery device of FIG. 3G, in an eighth state.

FIG. 3H shows the medicament delivery device 200 of FIG. 3G in a eighth state, after the user has removed the needle unit tool 710 from the medicament delivery device 200 and again pressed the distal end 120 of the needle cover 113 against an injection site (which may be the same injection site as previous, or a different injection site), to move the needle cover 113 from its extended position to its retracted position. Proximal movement of the needle cover 113 has caused the needle cover guide 143 to be rotated (e.g., in a similar manner as described previously in relation to FIGS. 6A and 6B, but this time by movement of the guide protrusions 620a, 620b through the respective first regions 641 of respective track portions 630b and 630d, rather than track portions 630a and 630c). Proximal movement of the needle cover 113 has also moved the actuation member latch from its locked configuration to its unlocked configuration (e.g., in a similar manner as described previously in relation to FIGS. FIGS. 4A and 4B).

To initiate delivery of a second dose of medicament 115, the user actuates the actuation member 404 from its first axial position to its second axial position by pushing the button 410 distally (e.g., in a similar manner as described previously in relation to FIG. 5D). Movement of the actuation member 404 from its first position to its second position initiates delivery of the second dose of medicament by moving the ratchet mechanism 505 from its second configuration to its third configuration (e.g., in a similar manner as described previously in relation to FIGS. 5D and 5E).

Figure 3I:
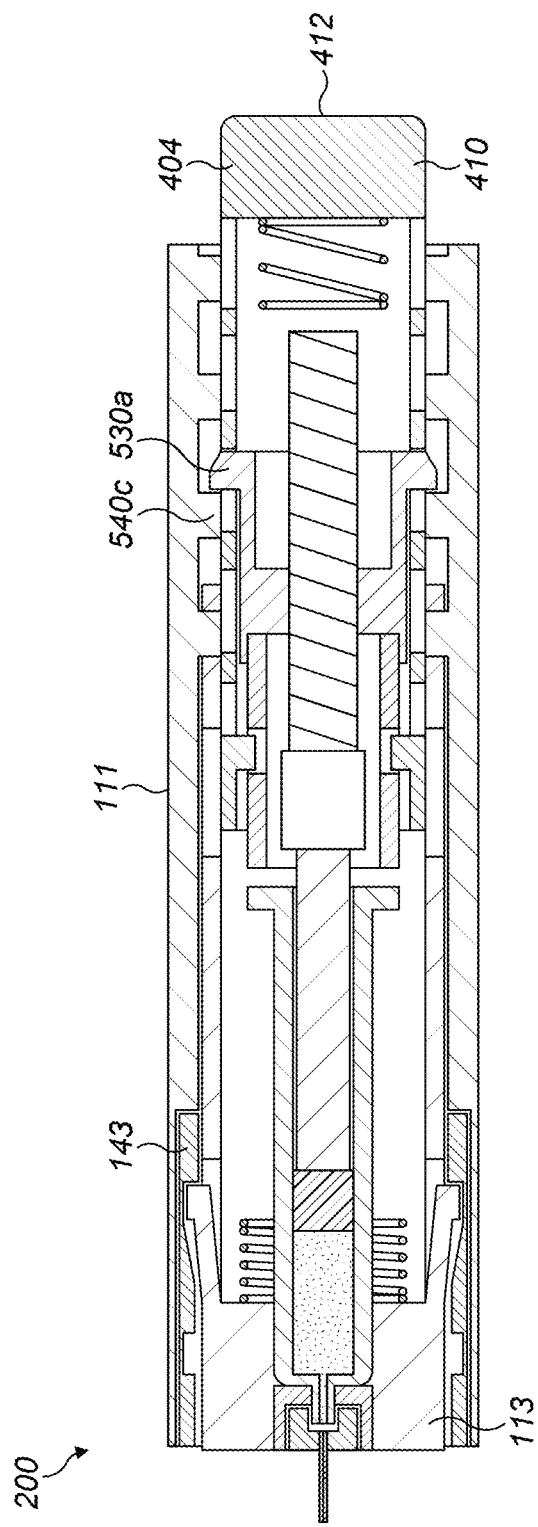
FIG. 3I is a schematic cross-sectional view of the medicament delivery device of FIG. 3H, in a ninth state.

FIG. 3I shows the medicament delivery device 200 of FIG. 3H in a ninth state, after the user has actuated and then released the actuation member 404 to dispense the second dose of medicament 115. FIG. 3I shows the ratchet mechanism 505 in its third configuration, with the ratchet collar 510 prevented from moving distally by engagement between the protrusion 530a and the third engagement feature 540c of the first engagement track 545a.

After the second dose of medicament has been delivered, the user may remove the medicament delivery device 200 from the injection site (e.g., in a similar manner as described previously in relation to FIG. 3E), which may cause the needle cover guide 143 to be rotated such that the needle cover 113 is locked in its extended state by a further locking element 690 of the needle cover guide 143 (e.g., in a similar manner as described previously in relation to FIG. 6C).

The user may then repeat the process of replacing the needle unit 116 with another new needle unit 116 using the needle unit tool 710 (e.g., in a similar manner as described previously in relation to any of FIGS. 3F, 3G, 6D and 6E), rotating the needle cover guide 143 in the process and thereby unlocking the needle cover 113 such that it can be moved proximally.

To deliver a third dose of medicament 115, the user again presses the distal end 120 of the needle cover 113 against an injection site (which may be the same injection site(s) as previous, or a different injection site), to move the needle cover 113 from its extended position to its retracted position. Proximal movement of the needle cover 113 again causes the needle cover guide 143 to be rotated (e.g., in a similar manner as described previously in relation to FIGS. 6A and 6B) and moves the actuation member latch 450 from its locked configuration to its unlocked configuration (e.g., in a similar manner as described previously in relation to FIGS. 4A and 4B).

To initiate delivery of the third dose of medicament 115, the user actuates the actuation member 404 from its first axial position to its second axial position by pushing the button 410 distally (e.g., in a similar manner as described previously in relation to FIGS. 5E and 5F). Movement of the actuation member 404 from its first position to its second position initiates delivery of the third dose of medicament 115 by moving the ratchet mechanism 505 from its third configuration to its fourth configuration (e.g., in a similar manner as described previously in relation to FIGS. 5F and 5G), releasing the ratchet collar 510 for axial movement to cause the third dose of medicament 115 to be dispensed.

Figure 3J:
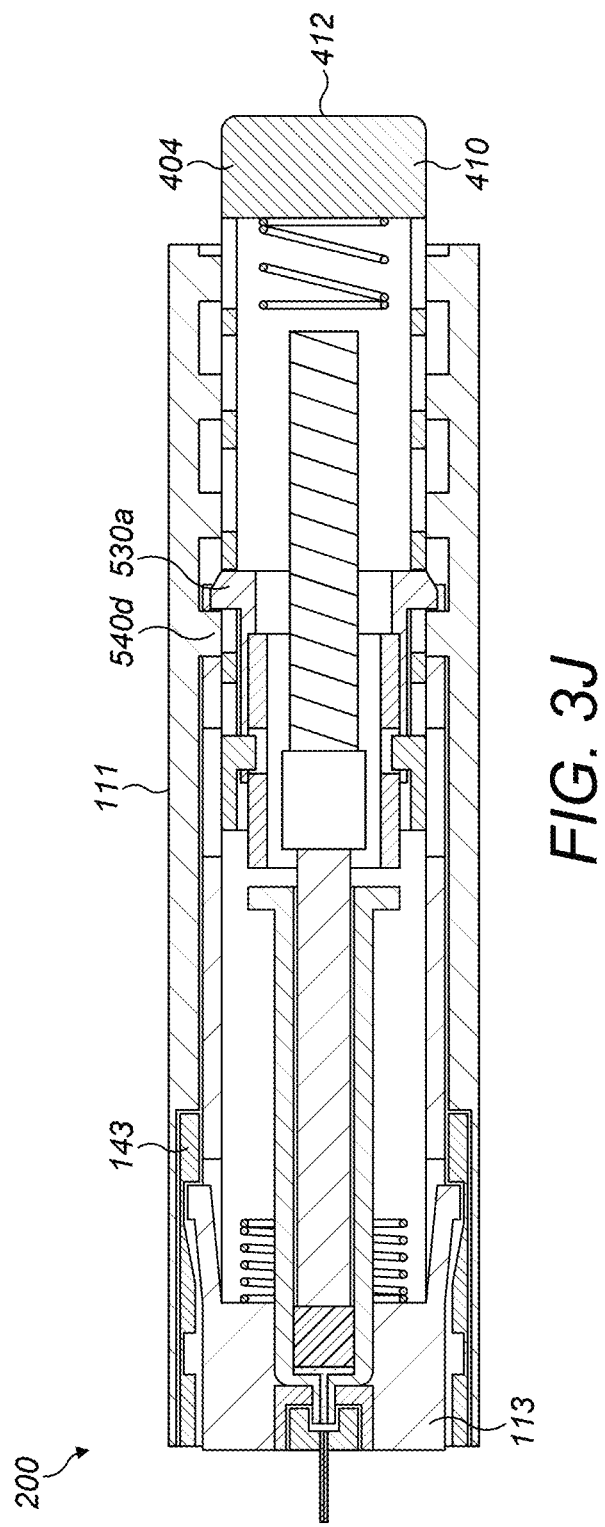
FIG. 3J is a schematic cross-sectional view of the medicament delivery device of FIG. 3I, in a tenth state.

FIG. 3J shows the medicament delivery device 200 of FIG. 3I in a tenth state, after the user has dispensed the third dose of medicament 115. In this example, the third dose of medicament 115 is the final dose of medicament to be administered using the medicament delivery device 200. The ratchet mechanism 505 is in its fourth configuration.

FIG. 3J shows the protrusion 530a having engaged a fourth engagement element 540a to limit further distal movement of the ratchet collar 510. However, this is not meant to be limiting. In one or more other examples, the protrusion 530a does not engage a fourth engagement element 540a to limit further distal movement of the ratchet collar 510. Instead, further distal movement of the ratchet collar 510 may limited by a different mechanism, for example the drive member may no longer provide a biasing force to rotate the rotary collar 119 after the final dose has been dispensed, or the plunger 121 may engage a stop feature that limits further distal movement of the plunger 121

Figure 3K:
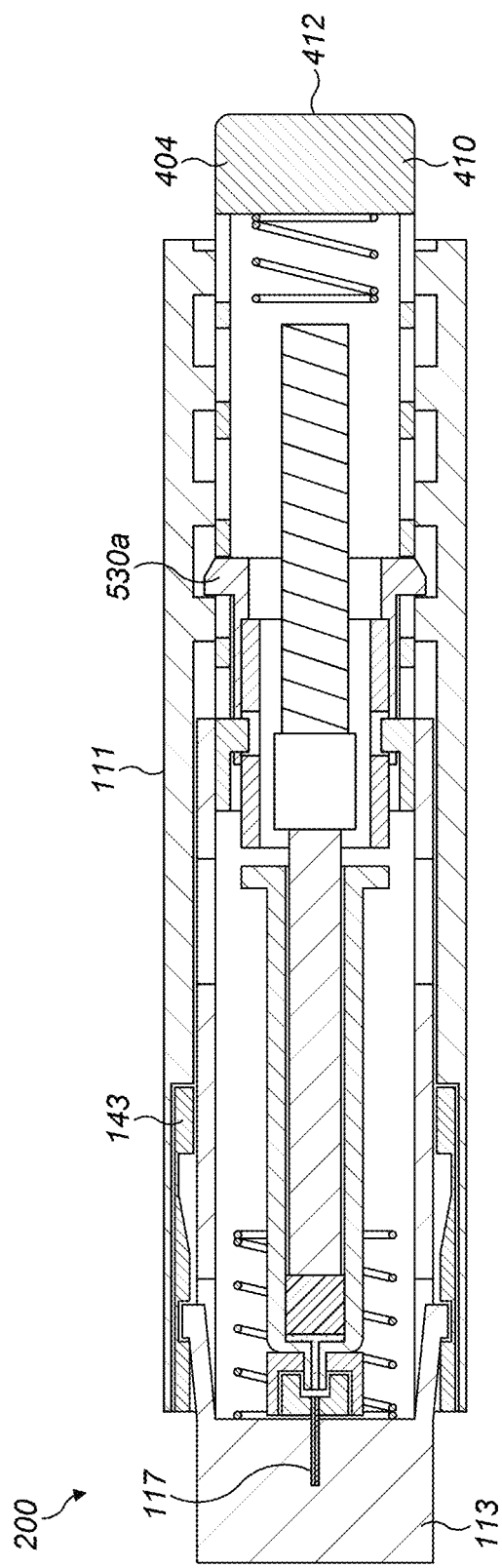
FIG. 3K is a schematic cross-sectional view of the medicament delivery device of FIG. 3J, in an eleventh state.

FIG. 3K shows the medicament delivery device 200 of FIG. 3J in a eleventh state, after the user has removed the medicament delivery device 200 from the injection site and the needle cover 113 has moved distally from its retracted position shown in FIG. 3J to its extended position shown in FIG. 3K (e.g., due to biasing by the needle cover biasing member 118). After the needle cover 113 has moved distally from its retracted position to its extended position, subsequent movement of the needle cover 113 from the extended position to the retracted position may once again be limited (e.g., by a locking element 690). However, unlike in previous instances in which the needle cover guide 143 has been rotated using the needle unit tool 710 to allow the needle cover 113 to be moved proximally again, the needle cover guide 143 is now inhibited from being rotated by to unlock the needle cover 113, as shown in FIG. 6F. The needle cover 113 therefore remains in a locked, extended position, protecting the user from the used needle 117.

FIG. 6F shows the needle cover guide 143 of the medicament delivery device 200 of FIG. 3K. Distal movement of the guide protrusion 620 as the needle cover 113 has moved from its retracted position to its extended position after delivery of the third dose has caused the guide protrusion 620 to engage a locking element 690 arranged between the third track portion 630c and the fourth track portion 630d (e.g., in a similar manner as described previously in relation to FIG. 6C). However, rotation of the needle cover 113 relative to the needle sleeve 113 is now limited (e.g., prevented) by a rotation stop element 695 (e.g., a wall) in the fourth track portion 630d). An attempt to rotate the needle cover guide 143 relative to the needle cover 113 (e.g., using a needle unit tool 710 as described previously) will cause the guide protrusion 620 to engage the rotation stop element 695, limiting rotation of the needle cover 113 relative to the needle sleeve 113. The needle cover guide 143 may therefore no longer be rotated to unlock the needle cover 113 for proximal movement.

The user may now safely dispose the medicament delivery device 200.

Figure 7:
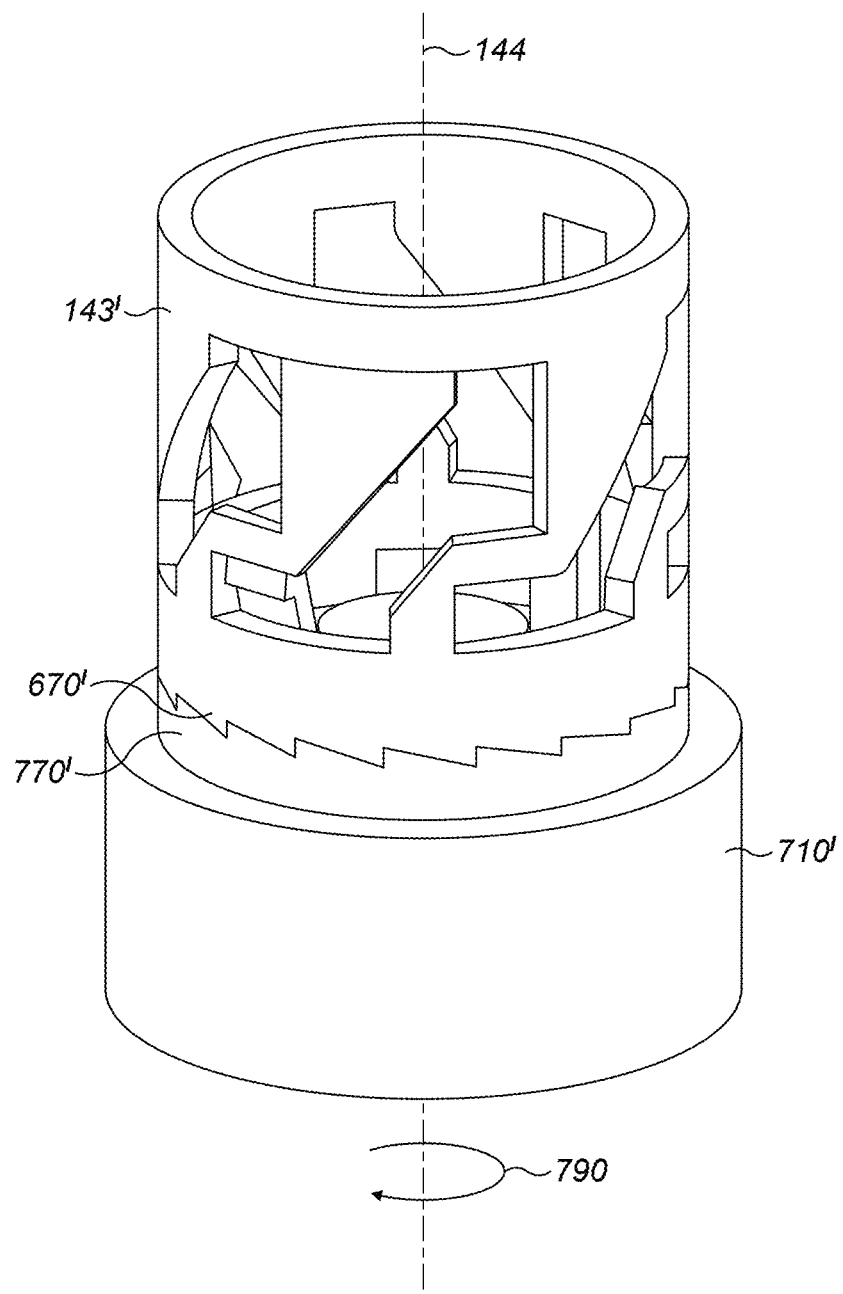
FIG. 7 is a perspective view of a needle cover guide, a needle unit tool and a portion of a needle cover, in accordance with one or more embodiments.

FIG. 7 shows an alternative embodiment of the needle unit tool 710', coupled to a needle cover guide 143' (which may be similar or identical to the needle cover guide 143). The needle unit tool 710' may share one or more feature with any needle unit tool 710 disclosed previously. However, the needle unit tool 710' has a tool engagement feature 770' comprising a ratchet gear rack formed from a plurality of asymmetrical ratchet teeth 774 arranged in a continuous circular pattern on a proximal-facing surface of the needle unit tool 710'.

Each tooth of the ratchet teeth 774 comprises a gently ramped surface 776 that each extend in a plane substantially normal to the axis 144, and a contact surface 778 that each extend in a plane substantially parallel to the axis 144. The ratchet gear rack of the needle unit tool 710' is configured to engage a corresponding tool engagement feature 670' of the needle cover guide 143', also in the form of a ratchet gear rack comprising a plurality of asymmetrical ratchet teeth 674. The ratchet teeth 674 are arranged in a continuous circular pattern on a distal-facing surface of the needle cover guide 143'. Each tooth of the ratchet teeth 674 comprises a gently ramped surface 676 that each extend in a plane substantially normal to the axis 144, and a contact surface 678 that each extend in a plane substantially parallel to the axis 144. The ratchet teeth 774 of the needle unit tool 710' and the ratchet teeth 674 of the needle cover guide 143' are arranged to engage with each other when the needle unit tool 710' is coupled to the needle cover guide 143', with the ramped surfaces 776 each engaging a respective ramped surface 676 and the contact surfaces 778 each engaging a respective contact surface 678.

The tool engagement feature 770' of the needle unit tool 710' and the tool engagement feature 670' of the needle cover guide 143 are therefore configured such that, when the tool engagement feature 770' and tool engagement feature 670' are coupled as shown in FIG. 7, rotation of the needle cover tool 710' relative to the body 111 in a first direction about the axis 144 (e.g. as shown by arrow 790) causes the needle cover guide 143' to rotate in concert with the needle cover tool 710', but rotation of the needle cover tool 710' relative to the body 111 in a second direction opposite to the first direction does not cause the needle cover guide 143' to substantially rotate relative to the body 111 (due to the ramped surfaces 676, 776 sliding over one another). Such a mechanism can allow the same needle unit tool 710' to be used for both coupling and uncoupling needle units 116 from the medicament delivery device 200 by screwing and unscrewing the needle units 116, but ensures that the needle cover guide 143' is only rotated by the rotation of the needle unit tool 710' in one of the two rotations (e.g., only during screwing on of a new needle unit 116).

Figure 8:
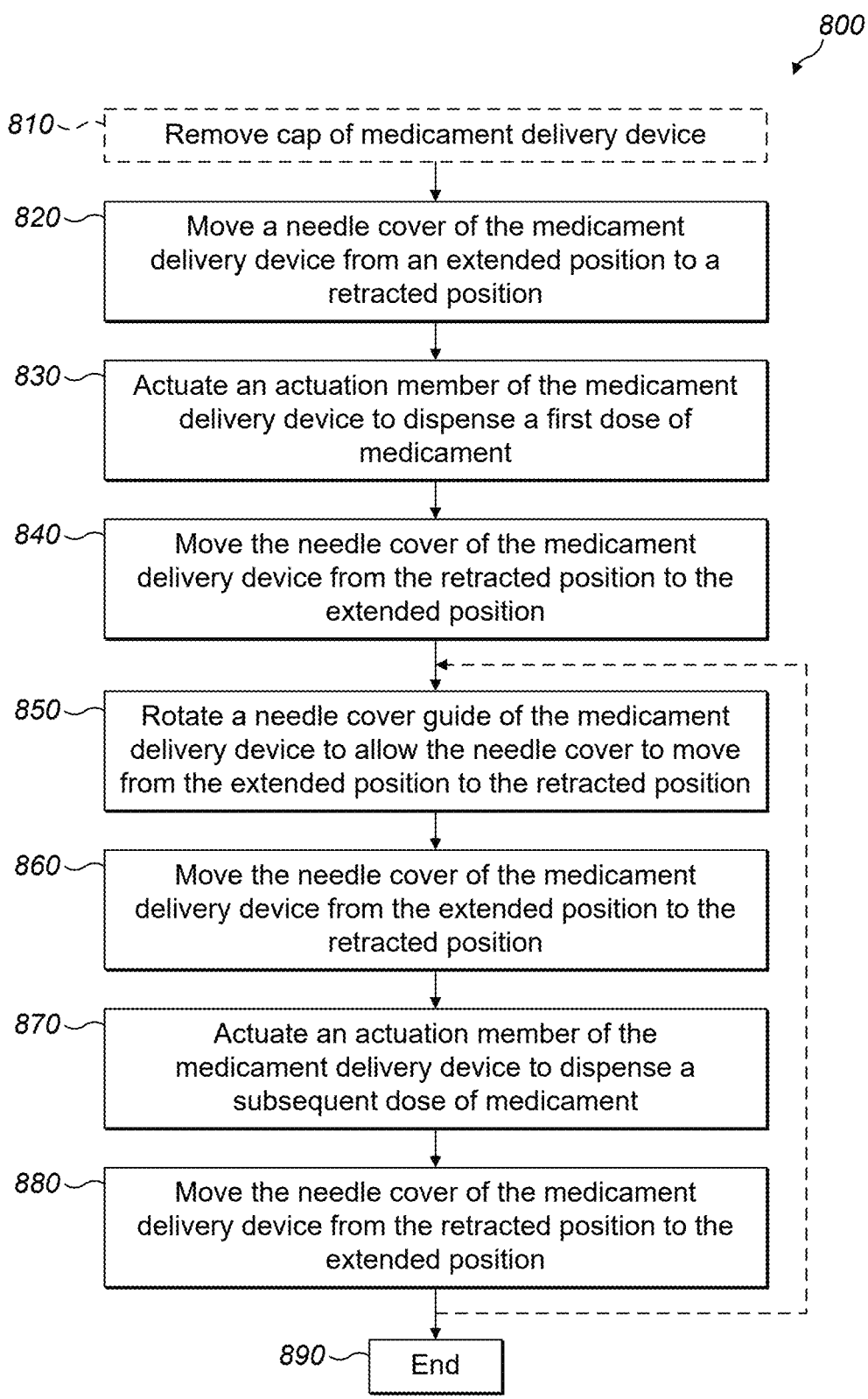
FIG. 8 is a flowchart illustrating a method of using a medicament delivery device in accordance with one or more embodiments.

A method 800 of using a medicament delivery device, which may be the medicament delivery device 200 described in relation to any of FIGS. 3A-3K, 4A-C, 5A-5G, 6A-6F and/or FIG. 7 will now be described with reference to FIG. 8.

At an optional operation 810, a cap 12 of the medicament delivery device 200 is removed (if present).

At operation 820, a needle cover 113 of the medicament delivery device is moved from an extended position to a retracted position. The needle cover 113 may be moved from the extended position to the retracted position by pressing the needle cover 113 against an injection site.

At operation 830, an actuation member 404 of the medicament delivery device is actuated to dispense a first dose of medicament (e.g., as previously described herein).

At operation 840, the needle cover 113 of the medicament delivery device is moved from the retracted position to the extended position (e.g., as previously described herein). The needle cover 113 may be moved from the retracted position to the extended position by removing the needle cover 113 from the injection site. Responsive to the needle cover 113 moving from the retracted position to the extended position, the needle cover 113 may be limited from moving from its extended position to its retracted position.

At operation 850, a needle cover guide 143 of the medicament delivery device is rotated to allow the needle cover 113 to move from its extended position to its retracted position. The needle cover guide 143 may be rotated using a needle unit tool 710, 710', for example during a needle unit replacement operation.

At operation 860, the needle cover 113 of the medicament delivery device is moved from the extended position to a retracted position. The needle cover 113 may be moved from the extended position to the retracted position by pressing the needle cover 113 against an injection site.

At operation 870, the actuation member 404 of the medicament delivery device is actuated to dispense a subsequent (e.g., second, third, . . . , etc.) dose of medicament (e.g., as previously described herein).

At optional operation 880, the needle cover 113 of the medicament delivery device is moved from the retracted position to the extended position (e.g., as previously described herein). The needle cover 113 may be moved from the retracted position to the extended position by removing the needle cover 113 from the injection site. Responsive to the needle cover 113 moving from the retracted position to the extended position, the needle cover 113 may be limited from moving from its extended position to its retracted position.

Optionally, after operation 880, operations 850 to 880 may be repeated one or more additional times in order to dispense further doses of medicament, if the medicament delivery device 200 is so configured (e.g., if rotation of the needle cover guide 143 is not yet limited by a rotation stop element 695).

At operation 890 the method 800 ends. Further rotation of the needle cover guide 143 may be limited by a rotation stop element 695.

While various aspects of this disclosure have been described as suitable for delivering a plurality of doses of a medicament into a subject, it should be understood that aspects of this disclosure may additionally/alternatively be used to dispense one or more doses of medicament without the medicament actually being injected into a subject, such as during a priming operation of the medicament delivery device. For example, in accordance with one or more aspects of this disclosure, a user may initiate movement of the medicament delivery mechanism by pushing the medicament delivery device into an injection site that is not part of a human or animal body (such as a block of rubber or foam), to trigger dispensing of a first dose of medicament into the non-human/non-animal injection site, wherein this first dose may be a priming dose that is not to be administered to a human or animal subject. A second priming dose may subsequently be administered to the non-human/non-animal injection site by the user removing and then reinserting the medicament delivery device into the human/non-animal injection site in accordance with one or more aspects disclosed herein. Further priming doses may be administered in a similar manner. Such a priming operation may be performed to flush the medicament through the syringe and/or needle, and/or as a test to check that the medicament delivery device is operating correctly.

While it has generally been described herein that the medicament delivery device 200 comprises both the ratchet mechanism 505 and the needle cover guide 143, it should be understood that in other examples the medicament delivery device 200 may comprise only one of the ratchet mechanism 505 and the needle cover guide 143. For example, the medicament delivery device 200 may employ a ratchet mechanism 505 for allowing discrete doses of medicament 115 to be dispensed, without also employing a needle cover guide 143 for locking the needle cover 113 after the delivery of each dose.

Alternatively, the medicament delivery device 200 may employ a needle cover guide 143 for locking the needle cover 113 after the needle cover 113 has moved from its retracted to its extended position, without also employing a ratchet mechanism 505 for allowing discrete doses of medicament 115 to be dispensed. In other words, in some examples the concept of the ratchet mechanism 505 and the needle cover guide 143 may be separable.

In any of the embodiments disclosed herein, the medicament delivery device 200 may additionally have a cap 12 which covers the distal end of the needle cover 113. The cap 12 may be coupled to the remainder of the medicament delivery device 200 (e.g., to the body 111) when the medicament delivery device 100 is in its initial state corresponding to FIG. 3A. The cap 12 may be removed from the remainder of the medicament delivery device 200 by the user, prior to injection. Removal of the cap 12 may also remove a rigid needle shield (RNS) surrounding the needle 117, wherein the RNS is removed with the cap 12 (e.g., due to engagement between the RNS and the cap 12).

It has generally been described herein that the needle cover guide 143 is rotated using a needle unit tool 710, during an operation of replacing (e.g. coupling or uncoupling) a needle unit 116. However, it should be understood that in other examples the needle cover guide 143 may be configured to be rotated in a different manner. For example, the needle cover guide 143 may be configured to be rotated during an operation that is not replacing the needle unit 116 (e.g., during attachment and/or removal of a cap 12 of the medicament delivery device 200, wherein the cap 12 comprises an engagement feature configured to engage the tool engagement feature 670 of needle cover guide for rotating the needle cover guide 143 as the cap 12 is rotated). In yet other examples, at least a portion of the needle cover guide 143 may be accessible to a user such that user may directly rotate the needle cover guide 143 with a finger.

It has generally been described herein that the engagement elements 540 each take the form of a projection such as a ridge, however this is not meant to be limiting. For example, in one or more alternative examples, the engagement elements 540 each take the form of a different type of projection to a ridge, or they take a form different to a projection, such as a recess. In each case, the engagement elements 540 each take a form that can be engaged by the protrusion 530 of the ratchet collar 510 to limit axial movement of the ratchet collar 510.

It has generally been described herein that the engagement elements 540 of each engagement track 545 are evenly spaced in the axial direction, which may lead to each dose of medicament being equal in size. However, it should be understood that in one or more other embodiments, the distance in the axial direction between each engagement element 540 in an engagement track 545 may vary between engagement elements 540, such that a different size of dose is dispensed as the protrusion 530 moves between the different engagement elements 540. For example, first, second and third engagement elements 540a, 540b, 540c may be arranged such that the distance along the axis 144 between the first engagement element 540a and the second engagement element 540b is greater than the distance along the axis 144 between the second engagement element 540b and the third engagement element 540c. As such, the first dose dispensed as the protrusion 530 of the ratchet collar 510 moves from the first engagement element 540a to the second engagement element 540b may be greater in size than the second dose dispensed as the protrusion 530 of the ratchet collar 510 moves from the second engagement element 540b to the third engagement element 540c, with the size of each dose being proportional to the distance between the two engagement elements used to dispense the dose (assuming the dose dispensed by the medicament delivery mechanism 180 is proportional to the axial distance moved by the ratchet collar 510).

It has generally been described herein that the actuation member 404 comprises a button 410, however this is not meant to be limiting. For example, in one or more alternative examples, the button 410 may be replaced by a slider or a rotatable dial, wherein the slider/rotatable dial is coupled to the arm(s) 420 of the actuation member 404 such that actuation of the actuation member 404 (e.g., via sliding of the slider or rotation of the dial by a user) causes distal and/or proximal movement of the arm(s) 420 for triggering delivery of a dose of medicament, in a similar manner as described elsewhere.

It should be understood that the actuation member 404 may be located at a different position relative to the body 111 to that described in relation to FIGS. 3A-3K. For example, in other examples the button 410 (or slider or dial) may be located at a different location than the proximal end of the body 111, for example at distal end of the body 111.

It has generally been described herein that the axially movable ratchet shuttle is in the form of a ratchet collar 510.

However, it should be understood that in other examples, a different form of ratchet shuttle could be used that comprises a flexible arm 520 and protrusion 530, and that can be moved axially by the drive member in a similar manner to the ratchet collar 510, but does not have the shape of a collar.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term, derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen.

The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without depart-

LIST OF REFERENCE NUMBERS

10—drug delivery device
11—housing
11a—window
12—cap assembly
13—needle sleeve
14—reservoir
15—medicament
17—needle
20—distal region
21—proximal region
22—button
23—bung or piston
100—medicament delivery device
111—body
113—needle cover
114—container
115—medicament
116—needle unit
117—needle
118—needle cover biasing member
119—rotary collar
120—distal end (of the needle cover)
121—plunger
122—external screw thread
123—bung or piston
124—drive member
125—internal screw thread
126—arm
127—protrusion (of needle cover guide)
128—track (of needle cover guide)
130—proximal end (of body)
131—distal end (of body)
140—distal end (of needle)
141—connection interface (of needle unit)
142—connection interface (of syringe)
143, 143'—needle cover guide
144—axis
150—syringe
152—arrow
171—spring
180—medicament delivery mechanism
200—medicament delivery device
400—medicament delivery device
404—actuation member
410—button
412—proximal actuation surface (of button)
420—arm (of actuation member)
430—apertures (of arm)
432—distal-facing surface (of aperture)
434—proximal-facing surface (of aperture)
440—guide surfaces (of arm)
450—actuation member latch
452—flexible extension (of actuation member latch)
454—projection (of actuation member latch)
456—recess (of latch element)
458—latch element
460—recess (of needle cover)
462—proximal-facing surface (of recess of latch element)
464—distal-facing surface (of projection)
466—proximal-facing surface (of recess of needle cover)
500—medicament delivery device
505—ratchet mechanism
510—ratchet collar
520—flexible arm (of ratchet collar)
530—protrusion (of ratchet collar)
532—engaging surface (of ratchet collar)
534—ramped surface (of ratchet collar)
540—engagement elements
542—engaging surface (of engagement element)
545—engagement track
610—guide extensions
620—guide protrusion
630a-630f—track portion(s)
641—first region
642—second region
643—third region
651—first position
652—second position
653—third position
654—fourth position
660—surface (of second region)
670, 670'—tool engagement feature (of needle cover guide)
672—teeth (of needle cover guide)
674—teeth (of ratchet gear rack)
676—ramped surface (of teeth)
678—contact surface (of teeth)
680—angled proximal wall (of first region)
682—arrow
684—arrow
686—arrow
690—locking element
692—locking surface (of locking element)
694—ramped surface (of locking element)
695—rotation stop element
710, 710'—needle unit tool
722—needle unit holder
770, 770'—tool engagement feature (of needle unit tool)
772—teeth (of needle unit tool)
774—teeth (of ratchet gear rack)
776—ramped surface (of teeth)
778—contact surface (of teeth)
790—arrow
800—method
810—first method operation
820—second method operation
830—third method operation
840—fourth method operation
850—fifth method operation
860—sixth method operation
870—seventh method operation
880—eighth method operation
890—ninth method operation

The invention claimed is:

1. A medicament delivery device comprising:
a body having a proximal end and a distal end arranged along a first axis, the body configured to hold a container containing a medicament;
a needle cover axially movable relative to the body between an extended position and a retracted position;
a medicament delivery mechanism comprising a plunger and a drive member, the drive member configured to move the plunger along the first axis to dispense the medicament from the container;
an actuation member configured to be actuated relative to the body; and
a ratchet mechanism coupled to the medicament delivery mechanism and sequentially movable between a first configuration, a second configuration and a third configuration, wherein the ratchet mechanism comprises:
a ratchet shuttle axially movable by the drive member and comprising a protrusion, and
an engagement track comprising a first engagement element and a second engagement element aligned along an inner surface of the body and along a second axis parallel to the first axis,
wherein the protrusion is configured to engage the first engagement element when the ratchet mechanism is in the first configuration, to limit axial movement of the ratchet shuttle by the drive member,
wherein the actuation member and the ratchet mechanism are arranged such that:
a first actuation of the actuation member moves the ratchet mechanism from the first configuration to the second configuration to cause a first dose of the medicament to be dispensed, and
a second actuation of the actuation member, subsequent to the first actuation, moves the ratchet mechanism from the second configuration to the third configuration to cause a second dose of the medicament to be dispensed.

2. The medicament delivery device of claim 1, wherein the actuation member comprises a button arranged to be pushed a first time to provide the first actuation and pushed a second time to provide the second actuation.

3. The medicament delivery device of claim 1, wherein the actuation member is movable between a first position and a second position, wherein the first actuation of the actuation member comprises a first movement of the actuation member from the first position to the second position, and wherein the second actuation of the actuation member comprises a second movement of the actuation member from the first position to the second position, the second movement subsequent to the first movement.

4. The medicament delivery device of claim 1, wherein the protrusion is configured to engage the second engagement element when the ratchet mechanism is in the second configuration, to limit axial movement of the ratchet shuttle by the drive member.

5. The medicament delivery device of claim 1, further comprising an arm that comprises a plurality of apertures and a plurality of guide surfaces arranged such that the apertures and guide surfaces alternate in an axial direction.

6. The medicament delivery device of claim 1, wherein the ratchet shuttle is a ratchet collar.

7. The medicament delivery device of claim 1, wherein the actuation member and ratchet mechanism are configured such that:
the first actuation of the actuation member disengages the protrusion from the first engagement element to cause the protrusion to move axially to the second engagement element; and
the second actuation of the actuation member disengages the protrusion from the second engagement element to cause the protrusion to move axially.

8. The medicament delivery device of claim 1, wherein:
when in the extended position, a distal end of the needle cover is distal to a distal end of a needle; and
when in the retracted position, the distal end of the needle is distal to the distal end of the needle cover.

9. The medicament delivery device of claim 8, wherein the medicament delivery device further comprises a needle cover biasing member configured to bias the needle cover distally.

10. The medicament delivery device of claim 8, further comprising a needle cover guide having a track configured to be engaged by a guide protrusion of the needle cover such that an axial movement of the needle cover from the extended position to the retracted position causes a rotation of the needle cover guide relative to the needle cover.

11. The medicament delivery device of claim 10, wherein the track comprises a locking element arranged such that an axial movement of the needle cover from the retracted position to the extended position subsequent to the rotation of the needle cover guide engages the guide protrusion with the locking element, to limit a further axial movement of the needle cover from the extended position to the retracted position.

12. The medicament delivery device of claim 11, wherein a further rotation of the needle cover guide relative to the needle cover disengages the guide protrusion from the locking element to allow the further axial movement of the needle cover from the extended position to the retracted position.

13. The medicament delivery device of claim 12, further comprising:
a needle unit comprising a needle;
a needle unit tool releasably coupled to the needle cover guide;
wherein the medicament delivery device is configured to be releasably coupled to the needle unit comprising a needle, and
wherein the needle cover guide is configured such that the further rotation is performed as the needle unit is coupled or uncoupled from the medicament delivery device by the needle unit tool.

14. The medicament delivery device of claim 1, further comprising an actuation member latch movable between a locked configuration, in which actuation of the actuation member is limited, and an unlocked configuration, in which actuation of the actuation member is allowed.

15. The medicament delivery device of claim 14, wherein the actuation member latch is configured to be moved from the locked configuration to the unlocked configuration by movement of the needle cover from the extended position to the retracted position.

16. The medicament delivery device of claim 1, wherein the actuation member and the ratchet mechanism are arranged such that:
a third actuation of the actuation member moves the ratchet mechanism from the third configuration to a fourth configuration to cause a third dose of the medicament to be dispensed.

17. The medicament delivery device according to claim 1, further comprising the medicament.

18. A system comprising:
a medicament delivery device comprising:
a body having a proximal end and a distal end arranged along a first axis, the body configured to hold a container containing a medicament;
a needle cover axially movable relative to the body between an extended position and a retracted position;
a medicament delivery mechanism comprising a plunger and a drive member, the drive member configured to move the plunger along the first axis to dispense the medicament from the container;
an actuation member configured to be actuated relative to the body; and
a ratchet mechanism coupled to the medicament delivery mechanism and sequentially movable between a first configuration, a second configuration and a third configuration, wherein the ratchet mechanism comprises:
- a ratchet shuttle axially movable by the drive member and comprising a protrusion, and
- an engagement track comprising a first engagement element and a second engagement element aligned along an inner surface of the body and along a second axis parallel to the first axis,
- wherein the protrusion is configured to engage the first engagement element when the ratchet mechanism is in the first configuration, to limit axial movement of the ratchet shuttle by the drive member, wherein the actuation member and the ratchet mechanism are arranged such that:
- a first actuation of the actuation member moves the ratchet mechanism from the first configuration to the second configuration to cause a first dose of the medicament to be dispensed, and
- a second actuation of the actuation member, subsequent to the first actuation, moves the ratchet mechanism from the second configuration to the third configuration to cause a second dose of the medicament to be dispensed;

a needle unit releasably couplable to the medicament delivery device; and a needle unit tool for coupling the needle unit to the medicament delivery device or uncoupling the needle unit from the medicament delivery device.

19. A method of operating a medicament delivery device, wherein the medicament delivery device comprises:
- a body having a proximal end and a distal end arranged along a first axis, the body configured to hold a container containing a medicament;
- a needle cover axially movable relative to the body between an extended position and a retracted position;
- a medicament delivery mechanism comprising a plunger and a drive member, the drive member configured to move the plunger along the first axis to dispense the medicament from the container;
- an actuation member configured to be actuated relative to the body; and
- a ratchet mechanism coupled to the medicament delivery mechanism and sequentially movable between a first configuration, a second configuration and a third configuration, wherein the ratchet mechanism comprises:
  - a ratchet shuttle axially movable by the drive member and comprising a protrusion, and
  - an engagement track comprising a first engagement element and a second engagement element aligned along an inner surface of the body and along a second axis parallel to the first axis,
  - wherein the protrusion is configured to engage the first engagement element when the ratchet mechanism is in the first configuration, to limit axial movement of the ratchet shuttle by the drive member, wherein the actuation member and the ratchet mechanism are arranged such that:
- a first actuation of the actuation member moves the ratchet mechanism from the first configuration to the second configuration to cause a first dose of the medicament to be dispensed, and
- a second actuation of the actuation member, subsequent to the first actuation, moves the ratchet mechanism from the second configuration to the third configuration to cause a second dose of the medicament to be dispensed;

wherein the method comprises:
- actuating the actuation member of the medicament delivery device to dispense a first dose of the medicament; and
- subsequent to actuating the actuation member of the medicament delivery device to dispense the first dose of the medicament, actuating the actuation member of the medicament delivery device to dispense a second dose of medicament.

* * * * *